US012648848B2

(12) United States Patent
Yushtein

(10) Patent No.: US 12,648,848 B2
(45) Date of Patent: Jun. 9, 2026

(54) EXPANSION AND LOCKING MECHANISM FOR MECHANICALLY EXPANDABLE VALVES

(71) Applicant: Edwards Lifesciences Corporation, Irvine, CA (US)

(72) Inventor: Haim Yushtein, Netanya (IL)

(73) Assignee: Edwards Lifesciences Corporation, Irvine, CA (US)

( * ) Notice: Subject to any disclaimer, the term of this patent is extended or adjusted under 35 U.S.C. 154(b) by 966 days.

(21) Appl. No.: 17/861,024

(22) Filed: Jul. 8, 2022

(65) Prior Publication Data

US 2022/0338978 A1 Oct. 27, 2022

Related U.S. Application Data

(63) Continuation of application No. PCT/US2021/012615, filed on Jan. 8, 2021.
(Continued)

(51) Int. Cl.
*A61F 2/24* (2006.01)
(52) U.S. Cl.
CPC ............ *A61F 2/243* (2013.01); *A61F 2/2418* (2013.01); *A61F 2220/0091* (2013.01)
(58) Field of Classification Search
CPC .......... A61F 2/24; A61F 2/2427; A61F 2/243; A61F 2/86
See application file for complete search history.

(56) References Cited

U.S. PATENT DOCUMENTS 3,409,013 A 11/1968 Berry
3,548,417 A 12/1970 Ronnie et al.
(Continued)

FOREIGN PATENT DOCUMENTS

DE 0144167 C 9/1903
DE 2246526 A1 3/1973
(Continued)

OTHER PUBLICATIONS

H.R. Andersen, et al. "Transluminal Implantation of Artificial Heart Valve. Description of a New Expandable Aortic Valve and Initial Results with implantation by Catheter Technique in Closed Chest Pig," European Heart Journal, No. 13. pp. 704-708. 1992.
(Continued)

*Primary Examiner* — Christopher D. Prone
(74) *Attorney, Agent, or Firm* — Klarquist Sparkman, LLP

(57) ABSTRACT

An implantable prosthetic device can include a radially expandable and compressible frame including an inflow end portion and an outflow end portion. The frame including a plurality of struts, and at least one expansion and locking mechanism having a first member, a second member extending at least partially into the first member, and a third member. The third member can include an engagement portion. The plurality of struts can include a first strut and a second strut pivotably coupled to one another to form an apex, the first strut having a first flange and the second strut having a second flange. When the frame is expanded, distal advancement of the third member can position the engagement member between the first and second flanges such that they engage the engagement member to resist pivoting of the first and second struts relative to one another to resist compression of the frame.

20 Claims, 17 Drawing Sheets

Related U.S. Application Data

(60) Provisional application No. 62/961,043, filed on Jan. 14, 2020.

(56)                    References Cited

U.S. PATENT DOCUMENTS

| | | |
|---|---|---|
| 3,587,115 A | 6/1971 | Donald |
| 3,657,744 A | 4/1972 | Ersek |
| 3,671,979 A | 6/1972 | Moulopoulos |
| 3,714,671 A | 2/1973 | Edwards et al. |
| 3,755,823 A | 9/1973 | Hancock |
| 4,035,849 A | 7/1977 | Angell et al. |
| 4,056,854 A | 11/1977 | Boretos et al. |
| 4,106,129 A | 8/1978 | Carpentier et al. |
| 4,222,126 A | 9/1980 | Boretos et al. |
| 4,265,694 A | 5/1981 | Boretos et al. |
| 4,297,749 A | 11/1981 | Davis et al. |
| RE30,912 E | 4/1982 | Hancock |
| 4,339,831 A | 7/1982 | Johnson |
| 4,343,048 A | 8/1982 | Ross et al. |
| 4,345,340 A | 8/1982 | Rosen |
| 4,373,216 A | 2/1983 | Klawitter |
| 4,406,022 A | 9/1983 | Roy |
| 4,441,216 A | 4/1984 | Ionescu et al. |
| 4,470,157 A | 9/1984 | Love |
| 4,535,483 A | 8/1985 | Klawitter et al. |
| 4,574,803 A | 3/1986 | Storz |
| 4,592,340 A | 6/1986 | Boyles |
| 4,605,407 A | 8/1986 | Black et al. |
| 4,612,011 A | 9/1986 | Kautzky |
| 4,643,732 A | 2/1987 | Pietsch et al. |
| 4,655,771 A | 4/1987 | Wallsten |
| 4,692,164 A | 9/1987 | Dzemeshkevich et al. |
| 4,733,665 A | 3/1988 | Palmaz |
| 4,759,758 A | 7/1988 | Gabbay |
| 4,762,128 A | 8/1988 | Rosenbluth |
| 4,777,951 A | 10/1988 | Cribier et al. |
| 4,787,899 A | 11/1988 | Lazarus |
| 4,787,901 A | 11/1988 | Baykut |
| 4,796,629 A | 1/1989 | Grayzel |
| 4,820,299 A | 4/1989 | Philippe et al. |
| 4,829,990 A | 5/1989 | Thuroff et al. |
| 4,851,001 A | 7/1989 | Taheri |
| 4,856,516 A | 8/1989 | Hillstead |
| 4,878,495 A | 11/1989 | Grayzel |
| 4,878,906 A | 11/1989 | Lindemann et al. |
| 4,883,458 A | 11/1989 | Shiber |
| 4,922,905 A | 5/1990 | Strecker |
| 4,966,604 A | 10/1990 | Reiss |
| 4,979,939 A | 12/1990 | Shiber |
| 4,986,830 A | 1/1991 | Owens et al. |
| 4,994,077 A | 2/1991 | Dobben |
| 5,007,896 A | 4/1991 | Shiber |
| 5,026,366 A | 6/1991 | Leckrone |
| 5,032,128 A | 7/1991 | Alonso |
| 5,037,434 A | 8/1991 | Lane |
| 5,047,041 A | 9/1991 | Samuels |
| 5,059,177 A | 10/1991 | Towne et al. |
| 5,080,668 A | 1/1992 | Bolz et al. |
| 5,085,635 A | 2/1992 | Cragg |
| 5,089,015 A | 2/1992 | Ross |
| 5,152,771 A | 10/1992 | Sabbaghian et al. |
| 5,163,953 A | 11/1992 | Vince |
| 5,167,628 A | 12/1992 | Boyles |
| 5,192,297 A | 3/1993 | Hull |
| 5,266,073 A | 11/1993 | Wall |
| 5,282,847 A | 2/1994 | Trescony et al. |
| 5,295,958 A | 3/1994 | Shturman |
| 5,332,402 A | 7/1994 | Teitelbaum |
| 5,360,444 A | 11/1994 | Kusuhara |
| 5,370,685 A | 12/1994 | Stevens |
| 5,397,351 A | 3/1995 | Pavcnik et al. |
| 5,411,055 A | 5/1995 | Kane |
| 5,411,552 A | 5/1995 | Andersen et al. |
| 5,443,446 A | 8/1995 | Shturman |
| 5,480,424 A | 1/1996 | Cox |
| 5,500,014 A | 3/1996 | Quijano et al. |
| 5,545,209 A | 8/1996 | Roberts et al. |
| 5,545,214 A | 8/1996 | Stevens |
| 5,549,665 A | 8/1996 | Vesely et al. |
| 5,554,185 A | 9/1996 | Block et al. |
| 5,558,644 A | 9/1996 | Boyd et al. |
| 5,571,175 A | 11/1996 | Vanney et al. |
| 5,584,803 A | 12/1996 | Stevens et al. |
| 5,591,185 A | 1/1997 | Kilmer et al. |
| 5,591,195 A | 1/1997 | Taheri et al. |
| 5,607,464 A | 3/1997 | Trescony et al. |
| 5,609,626 A | 3/1997 | Quijano et al. |
| 5,628,792 A | 5/1997 | Lentell |
| 5,639,274 A | 6/1997 | Fischell et al. |
| 5,665,115 A | 9/1997 | Cragg |
| 5,716,417 A | 2/1998 | Girard et al. |
| 5,728,068 A | 3/1998 | Leone et al. |
| 5,749,890 A | 5/1998 | Shaknovich |
| 5,756,476 A | 5/1998 | Epstein et al. |
| 5,769,812 A | 6/1998 | Stevens et al. |
| 5,800,508 A | 9/1998 | Goicoechea et al. |
| 5,840,081 A | 11/1998 | Andersen et al. |
| 5,855,597 A | 1/1999 | Jayaraman |
| 5,855,601 A | 1/1999 | Bessler et al. |
| 5,855,602 A | 1/1999 | Angell |
| 5,925,063 A | 7/1999 | Khosravi |
| 5,957,949 A | 9/1999 | Leonhardt et al. |
| 6,027,525 A | 2/2000 | Suh et al. |
| 6,132,473 A | 10/2000 | Williams et al. |
| 6,168,614 B1 | 1/2001 | Andersen et al. |
| 6,171,335 B1 | 1/2001 | Wheatley et al. |
| 6,174,327 B1 | 1/2001 | Mertens et al. |
| 6,210,408 B1 | 4/2001 | Chandrasekaran et al. |
| 6,217,585 B1 | 4/2001 | Houser et al. |
| 6,221,091 B1 | 4/2001 | Khosravi |
| 6,231,602 B1 | 5/2001 | Carpentier et al. |
| 6,245,102 B1 | 6/2001 | Jayaraman |
| 6,299,637 B1 | 10/2001 | Shaolian et al. |
| 6,302,906 B1 | 10/2001 | Goicoechea et al. |
| 6,338,740 B1 | 1/2002 | Carpentier |
| 6,350,277 B1 | 2/2002 | Kocur |
| 6,352,547 B1 | 3/2002 | Brown et al. |
| 6,425,916 B1 | 7/2002 | Garrison et al. |
| 6,440,764 B1 | 8/2002 | Focht et al. |
| 6,454,799 B1 | 9/2002 | Schreck |
| 6,458,153 B1 | 10/2002 | Bailey et al. |
| 6,461,382 B1 | 10/2002 | Cao |
| 6,468,660 B2 | 10/2002 | Ogle et al. |
| 6,482,228 B1 | 11/2002 | Norred |
| 6,488,704 B1 | 12/2002 | Connelly et al. |
| 6,527,979 B2 | 3/2003 | Constantz et al. |
| 6,569,196 B1 | 5/2003 | Vesely |
| 6,582,462 B1 | 6/2003 | Andersen et al. |
| 6,605,112 B1 | 8/2003 | Moll et al. |
| 6,652,578 B2 | 11/2003 | Bailey et al. |
| 6,689,123 B2 | 2/2004 | Pinchasik |
| 6,716,244 B2 | 4/2004 | Klaco |
| 6,730,118 B2 | 5/2004 | Spenser et al. |
| 6,733,525 B2 | 5/2004 | Yang et al. |
| 6,767,362 B2 | 7/2004 | Schreck |
| 6,769,161 B2 | 8/2004 | Brown et al. |
| 6,783,542 B2 | 8/2004 | Eidenschink |
| 6,830,584 B1 | 12/2004 | Seguin |
| 6,878,162 B2 | 4/2005 | Bales et al. |
| 6,893,460 B2 | 5/2005 | Spenser et al. |
| 6,908,481 B2 | 6/2005 | Cribier |
| 6,936,067 B2 | 8/2005 | Buchanan |
| 7,018,406 B2 | 3/2006 | Seguin et al. |
| 7,018,408 B2 | 3/2006 | Bailey et al. |
| 7,096,554 B2 | 8/2006 | Austin et al. |
| 7,225,518 B2 | 6/2007 | Eidenschink et al. |
| 7,276,078 B2 | 10/2007 | Spenser et al. |
| 7,276,084 B2 | 10/2007 | Yang et al. |
| 7,316,710 B1 | 1/2008 | Cheng et al. |
| 7,318,278 B2 | 1/2008 | Zhang et al. |
| 7,374,571 B2 | 5/2008 | Pease et al. |
| 7,393,360 B2 | 7/2008 | Spenser et al. |
| 7,445,631 B2 * | 11/2008 | Salahieh ............ A61F 2/2427 |
| | | 623/2.18 |

(56) References Cited

U.S. PATENT DOCUMENTS

| | | | |
|---|---|---|---|
| 7,462,191 B2 | 12/2008 | Spenser et al. |
| 7,510,575 B2 | 3/2009 | Spenser et al. |
| 7,563,280 B2 | 7/2009 | Anderson et al. |
| 7,585,321 B2 | 9/2009 | Cribier |
| 7,618,446 B2 | 11/2009 | Andersen et al. |
| 7,618,447 B2 | 11/2009 | Case et al. |
| 7,655,034 B2 | 2/2010 | Mitchell et al. |
| 7,785,366 B2 | 8/2010 | Maurer et al. |
| 7,959,665 B2 | 6/2011 | Pienknagura |
| 7,959,672 B2 | 6/2011 | Salahieh et al. |
| 7,993,394 B2 | 8/2011 | Hariton et al. |
| 8,029,556 B2 | 10/2011 | Rowe |
| 8,075,611 B2 | 12/2011 | Millwee et al. |
| 8,128,686 B2 | 3/2012 | Paul et al. |
| 8,167,932 B2 | 5/2012 | Bourang et al. |
| 8,291,570 B2 | 10/2012 | Eidenschink et al. |
| 8,348,998 B2 | 1/2013 | Pintor et al. |
| 8,449,606 B2 | 5/2013 | Eliasen et al. |
| 8,454,685 B2 | 6/2013 | Hariton et al. |
| 8,647,378 B2 * | 2/2014 | Mews ................... A61B 17/885 |
| | | 623/1.11 |
| 8,652,203 B2 | 2/2014 | Quadri et al. |
| 8,685,055 B2 | 4/2014 | VanTassel et al. |
| 8,747,463 B2 | 6/2014 | Fogarty et al. |
| 9,078,781 B2 | 7/2015 | Ryan et al. |
| 9,566,178 B2 * | 2/2017 | Cartledge ................ A61F 2/966 |
| 10,603,165 B2 * | 3/2020 | Maimon ................ A61F 2/2418 |
| 11,224,509 B2 | 1/2022 | Dasi et al. |
| 2001/0021872 A1 | 9/2001 | Bailey et al. |
| 2002/0026094 A1 | 2/2002 | Roth |
| 2002/0032481 A1 | 3/2002 | Gabbay |
| 2002/0138135 A1 | 9/2002 | Duerig et al. |
| 2002/0143390 A1 | 10/2002 | Ishii |
| 2002/0173842 A1 | 11/2002 | Buchanan |
| 2003/0014105 A1 | 1/2003 | Cao |
| 2003/0040791 A1 | 2/2003 | Oktay |
| 2003/0050694 A1 | 3/2003 | Yang et al. |
| 2003/0100939 A1 | 5/2003 | Yodfat et al. |
| 2003/0158597 A1 | 8/2003 | Quiachon et al. |
| 2003/0212454 A1 | 11/2003 | Scott et al. |
| 2004/0024452 A1 | 2/2004 | Kruse et al. |
| 2004/0039436 A1 | 2/2004 | Spenser et al. |
| 2004/0078074 A1 | 4/2004 | Anderson et al. |
| 2004/0186558 A1 | 9/2004 | Pavcnik et al. |
| 2004/0186563 A1 | 9/2004 | Lobbi |
| 2004/0186565 A1 | 9/2004 | Schreck |
| 2004/0260389 A1 | 12/2004 | Case et al. |
| 2005/0010285 A1 | 1/2005 | Lambrecht et al. |
| 2005/0075725 A1 | 4/2005 | Rowe |
| 2005/0075728 A1 | 4/2005 | Nguyen et al. |
| 2005/0096736 A1 | 5/2005 | Osse et al. |
| 2005/0096738 A1 | 5/2005 | Cali et al. |
| 2005/0137686 A1 | 6/2005 | Salahieh et al. |
| 2005/0188525 A1 | 9/2005 | Weber et al. |
| 2005/0203614 A1 | 9/2005 | Forster et al. |
| 2005/0203617 A1 | 9/2005 | Forster et al. |
| 2005/0234546 A1 | 10/2005 | Nugent et al. |
| 2006/0004469 A1 | 1/2006 | Sokel |
| 2006/0025857 A1 | 2/2006 | Bergheim et al. |
| 2006/0058872 A1 | 3/2006 | Salahieh et al. |
| 2006/0074484 A1 | 4/2006 | Huber |
| 2006/0108090 A1 | 5/2006 | Ederer et al. |
| 2006/0149350 A1 | 7/2006 | Patel et al. |
| 2006/0183383 A1 | 8/2006 | Asmus et al. |
| 2006/0229719 A1 | 10/2006 | Marquez et al. |
| 2006/0259136 A1 | 11/2006 | Nguyen et al. |
| 2006/0259137 A1 | 11/2006 | Artof et al. |
| 2006/0287717 A1 | 12/2006 | Rowe et al. |
| 2007/0005131 A1 | 1/2007 | Taylor |
| 2007/0010876 A1 | 1/2007 | Salahieh et al. |
| 2007/0010877 A1 | 1/2007 | Salahieh et al. |
| 2007/0112422 A1 | 5/2007 | Dehdashtian |
| 2007/0162102 A1 | 7/2007 | Ryan et al. |
| 2007/0203503 A1 | 8/2007 | Salahieh et al. |
| 2007/0203575 A1 | 8/2007 | Forster et al. |
| 2007/0203576 A1 | 8/2007 | Lee et al. |
| 2007/0208550 A1 | 9/2007 | Cao et al. |
| 2007/0213813 A1 | 9/2007 | Segesser et al. |
| 2007/0233228 A1 | 10/2007 | Eberhardt et al. |
| 2007/0260305 A1 | 11/2007 | Drews et al. |
| 2007/0265700 A1 | 11/2007 | Eliasen et al. |
| 2008/0021546 A1 | 1/2008 | Patz et al. |
| 2008/0114442 A1 | 5/2008 | Mitchell et al. |
| 2008/0125853 A1 | 5/2008 | Bailey et al. |
| 2008/0154355 A1 | 6/2008 | Benichou et al. |
| 2008/0183271 A1 | 7/2008 | Frawley et al. |
| 2008/0208327 A1 | 8/2008 | Rowe |
| 2008/0243245 A1 | 10/2008 | Thambar et al. |
| 2008/0255660 A1 | 10/2008 | Guyenot et al. |
| 2008/0275537 A1 | 11/2008 | Limon |
| 2008/0294248 A1 | 11/2008 | Yang et al. |
| 2009/0118826 A1 | 5/2009 | Khaghani |
| 2009/0125118 A1 | 5/2009 | Gong |
| 2009/0157175 A1 | 6/2009 | Benichou |
| 2009/0276040 A1 | 11/2009 | Rowe et al. |
| 2009/0281619 A1 | 11/2009 | Le et al. |
| 2009/0287296 A1 | 11/2009 | Manasse |
| 2009/0287299 A1 | 11/2009 | Tabor et al. |
| 2009/0299452 A1 | 12/2009 | Eidenschink et al. |
| 2009/0319037 A1 | 12/2009 | Rowe et al. |
| 2010/0004735 A1 | 1/2010 | Yang et al. |
| 2010/0049313 A1 | 2/2010 | Alon et al. |
| 2010/0082094 A1 | 4/2010 | Quadri et al. |
| 2010/0100176 A1 | 4/2010 | Elizondo et al. |
| 2010/0168844 A1 | 7/2010 | Toomes et al. |
| 2010/0185277 A1 | 7/2010 | Braido et al. |
| 2010/0198347 A1 | 8/2010 | Zakay et al. |
| 2010/0204781 A1 | 8/2010 | Alkhatib |
| 2011/0015729 A1 | 1/2011 | Jimenez et al. |
| 2011/0022157 A1 | 1/2011 | Essinger et al. |
| 2011/0066224 A1 | 3/2011 | White |
| 2011/0137397 A1 | 6/2011 | Chau et al. |
| 2011/0218619 A1 | 9/2011 | Benichou et al. |
| 2011/0319991 A1 | 12/2011 | Hariton et al. |
| 2012/0030090 A1 | 2/2012 | Johnston et al. |
| 2012/0089223 A1 | 4/2012 | Nguyen et al. |
| 2012/0101571 A1 | 4/2012 | Thambar et al. |
| 2012/0123529 A1 | 5/2012 | Levi et al. |
| 2012/0259409 A1 | 10/2012 | Nguyen et al. |
| 2013/0023985 A1 | 1/2013 | Khairkhahan et al. |
| 2013/0046373 A1 | 2/2013 | Cartledge et al. |
| 2013/0150956 A1 | 6/2013 | Yohanan et al. |
| 2013/0166017 A1 | 6/2013 | Cartledge et al. |
| 2013/0190857 A1 | 7/2013 | Mitra et al. |
| 2013/0274873 A1 | 10/2013 | Delaloye et al. |
| 2013/0310926 A1 | 11/2013 | Hariton |
| 2013/0317598 A1 | 11/2013 | Rowe et al. |
| 2013/0331929 A1 | 12/2013 | Mitra et al. |
| 2014/0194981 A1 | 7/2014 | Menk et al. |
| 2014/0200661 A1 | 7/2014 | Pintor et al. |
| 2014/0209238 A1 | 7/2014 | Bonyuet et al. |
| 2014/0222136 A1 | 8/2014 | Geist et al. |
| 2014/0277417 A1 | 9/2014 | Schraut et al. |
| 2014/0277419 A1 | 9/2014 | Garde et al. |
| 2014/0277424 A1 | 9/2014 | Oslund |
| 2014/0277563 A1 | 9/2014 | White |
| 2014/0296962 A1 | 10/2014 | Cartledge et al. |
| 2014/0330372 A1 | 11/2014 | Weston et al. |
| 2014/0343670 A1 | 11/2014 | Bakis et al. |
| 2014/0343671 A1 | 11/2014 | Yohanan et al. |
| 2014/0350667 A1 | 11/2014 | Braido et al. |
| 2015/0073545 A1 | 3/2015 | Braido |
| 2015/0073546 A1 | 3/2015 | Braido |
| 2015/0135506 A1 | 5/2015 | White |
| 2015/0157455 A1 | 6/2015 | Hoang et al. |
| 2016/0374802 A1 | 12/2016 | Levi et al. |
| 2017/0014229 A1 | 1/2017 | Nguyen-Thien-Nhon et al. |
| 2018/0028310 A1 | 2/2018 | Gurovich et al. |
| 2018/0153689 A1 | 6/2018 | Maimon et al. |
| 2018/0325665 A1 | 11/2018 | Gurovich et al. |
| 2018/0344456 A1 | 12/2018 | Barash et al. |
| 2019/0159894 A1 | 5/2019 | Levi et al. |

(56)                    References Cited

U.S. PATENT DOCUMENTS

| | | | |
|---|---|---|---|
| 2019/0192288 A1 | 6/2019 | Levi et al. |
| 2019/0192289 A1 | 6/2019 | Levi et al. |

FOREIGN PATENT DOCUMENTS

| | | |
|---|---|---|
| DE | 19532846 A1 | 3/1997 |
| DE | 19546692 A1 | 6/1997 |
| DE | 19857887 A1 | 7/2000 |
| DE | 19907646 A1 | 8/2000 |
| DE | 10049812 A1 | 4/2002 |
| DE | 10049813 C1 | 4/2002 |
| DE | 10049814 A1 | 4/2002 |
| DE | 10049815 A1 | 4/2002 |
| EP | 0103546 B1 | 5/1988 |
| EP | 0850607 A1 | 7/1998 |
| EP | 1057460 A1 | 12/2000 |
| EP | 1088529 A2 | 4/2001 |
| EP | 1570809 A1 | 9/2005 |
| FR | 2788217 A1 | 7/2000 |
| FR | 2815844 A1 | 5/2002 |
| GB | 2056023 A | 3/1981 |
| SU | 1271508 A1 | 11/1986 |
| WO | 1991017720 A1 | 11/1991 |
| WO | 1992017118 A1 | 10/1992 |
| WO | 1993001768 A1 | 2/1993 |
| WO | 1997024080 A1 | 7/1997 |
| WO | 1998029057 A1 | 7/1998 |
| WO | 1999030646 A1 | 6/1999 |
| WO | 1999033414 A1 | 7/1999 |
| WO | 1999040964 A1 | 8/1999 |
| WO | 1999047075 A1 | 9/1999 |
| WO | 2000018333 A1 | 4/2000 |
| WO | 2000041652 A1 | 7/2000 |
| WO | 2000047139 A1 | 8/2000 |
| WO | 2001035878 A2 | 5/2001 |
| WO | 2001049213 A2 | 7/2001 |
| WO | 2001054624 A1 | 8/2001 |
| WO | 2001054625 A1 | 8/2001 |
| WO | 2001062189 A1 | 8/2001 |
| WO | 2001064137 A1 | 9/2001 |
| WO | 2001076510 A2 | 10/2001 |
| WO | 2002022054 A1 | 3/2002 |
| WO | 2002036048 A1 | 5/2002 |
| WO | 2002041789 A2 | 5/2002 |
| WO | 2002043620 A1 | 6/2002 |
| WO | 2002047575 A2 | 6/2002 |
| WO | 2002049540 A2 | 6/2002 |
| WO | 2003047468 A1 | 6/2003 |
| WO | 2005034812 A1 | 4/2005 |
| WO | 2005055883 A1 | 6/2005 |
| WO | 2005084595 A1 | 9/2005 |
| WO | 2005102015 A2 | 11/2005 |
| WO | 2006014233 A2 | 2/2006 |
| WO | 2006032051 A2 | 3/2006 |
| WO | 2006034008 A2 | 3/2006 |
| WO | 2006111391 A1 | 10/2006 |
| WO | 2006127089 A1 | 11/2006 |
| WO | 2006138173 A2 | 12/2006 |
| WO | 2007047488 A2 | 4/2007 |
| WO | 2007067942 A1 | 6/2007 |
| WO | 2007097983 A2 | 8/2007 |
| WO | 2008005405 A2 | 1/2008 |
| WO | 2008015257 A2 | 2/2008 |
| WO | 2008035337 A2 | 3/2008 |
| WO | 2008091515 A2 | 7/2008 |
| WO | 2008147964 A1 | 12/2008 |
| WO | 2008150529 A1 | 12/2008 |
| WO | 2009033469 A1 | 3/2009 |
| WO | 2009042196 A2 | 4/2009 |
| WO | 2009053497 A1 | 4/2009 |
| WO | 2009061389 A2 | 5/2009 |
| WO | 2009094188 A2 | 7/2009 |
| WO | 2009116041 A2 | 9/2009 |
| WO | 2009149462 A2 | 12/2009 |
| WO | 2010011699 A2 | 1/2010 |
| WO | 2010121076 A2 | 10/2010 |
| WO | 2013106585 A1 | 7/2013 |
| WO | 2015085218 A1 | 6/2015 |

OTHER PUBLICATIONS

H.R. Andersen "History of Percutaneous Aortic Valve Prosthesis," Herz No. 34. pp. 343-346. 2009.

Pavcnik, et al. "Development and initial Experimental Evaluation of a Prosthetic Aortic Valve for Transcatheter Placement," Cardiovascular Radiology, vol. 183, No. 1. pp. 151-154. 1992.

Bailey, S. "Percutaneous Expandable Prosthetic Valves," Textbook of Interventional Cardiology vol. 2, 2nd Ed. pp. 1268-1276. 1994.

Al-Khaja, et al. "Eleven Years' Experience with Carpentier-Edwards Biological Valves in Relation to Survival and Complications," European Journal of Cardiothoracic Surgery, vol. 3. pp. 305-311. 1989.

Ross, "Aortic Valve Surgery," at a meeting of the Council on Aug. 4, 1966. pp. 192-197.

Sabbah, et al. "Mechanical Factors in the Degeneration of Porcine Bioprosthetic Valves: An Overview," Journal of Cardiac Surgery, vol. 4, No. 4. pp. 302-309. 1989.

Wheatley, "Valve Prostheses," Operative Surgery, 4th ed. pp. 415-424. 1986.

Uchida, "Modifications of Gianturco Expandable Wire Stents," American Journal of Roentgenology, vol. 150. pp. 1185-1187. 1986.

Walther T, Dehdashtian MM, Khanna R, Young E, Goldbrunner PJ, Lee W. Trans-catheter valve-in-valve implantation: in vitro hydro-dynamic performance of the SAPIEN+cloth trans-catheter heart valve in the Carpentier-Edwards Perimount valves. Eur J Cardiothorac Surg. 2011;40(5):1120-6. Epub Apr. 6, 2011.

Fontaine, M.D., Arthur B., et al., "Vascular Stent Prototype; Results of Preclinical Evaluation", p. 29-34; Technical Developments and Instrumentation; Jan.-Feb. 1996, vol. 7, No. 1.

Fontaine, M.D., Arthur B., et al., "Prototype Stent: Invivo Swine Studies in the Biliary System", p. 101-105, Journal of Vascular and Interventional Radiology; Jan.-Feb. 1997; vol. 8, No. 1.

Patrick W. Serruys, Nicolo Piazza, Alain Cribier, John Webb, Jean-Claude Laborde, Peter de Jaegere, "Transcatheter Aortic Valve Implantation: Tips and Tricks to Avoid Failure"; we file the table of contents and pp. 18 to 39 (Chapter 2) and pp. 102-114 (Chapter 8); the publication date according to the "Library of Congress Cataloging-in-Publication Data" is Nov. 24, 2009.

* cited by examiner

EXPANSION AND LOCKING MECHANISM FOR MECHANICALLY EXPANDABLE VALVES

CROSS REFERENCE TO RELATED APPLICATION

This application is a continuation of PCT Patent Application No. PCT/US2021/012615, entitled "EXPANSION AND LOCKING MECHANISM FOR MECHANICALLY EXPANDABLE VALVES," filed Jan. 8, 2021, which claims the benefit of U.S. Provisional Application No. 62/961,043, entitled "EXPANSION AND LOCKING MECHANISM FOR MECHANICALLY EXPANDABLE VALVES," filed on Jan. 14, 2020, all of which are incorporated by reference herein in their entirety.

FIELD

The present disclosure relates to implantable, mechanically expandable prosthetic devices, such as prosthetic heart valves, and to methods and delivery assemblies for, and including, such devices.

BACKGROUND

The human heart can suffer from various valvular diseases. These valvular diseases can result in significant malfunctioning of the heart and ultimately require repair of the native valve or replacement of the native valve with an artificial valve. There are a number of known repair devices (e.g., stents) and artificial valves, as well as a number of known methods of implanting these devices and valves in humans. Percutaneous and minimally-invasive surgical approaches are used in various procedures to deliver prosthetic medical devices to locations inside the body that are not readily accessible by surgery or where access without surgery is desirable. In one specific example, a prosthetic heart valve can be mounted in a crimped state on the distal end of a delivery apparatus and advanced through the patient's vasculature (e.g., through a femoral artery and the aorta) until the prosthetic heart valve reaches the implantation site in the heart. The prosthetic heart valve is then expanded to its functional size, for example, by inflating a balloon on which the prosthetic valve is mounted, actuating a mechanical actuator that applies an expansion force to the prosthetic heart valve, or by deploying the prosthetic heart valve from a sheath of the delivery apparatus so that the prosthetic heart valve can self-expand to its functional size.

Prosthetic heart valves that rely on a mechanical actuator for expansion can be referred to as "mechanically expandable" prosthetic heart valves. Mechanically expandable prosthetic heart valves can provide one or more advantages over self-expandable and balloon-expandable prosthetic heart valves. For example, mechanically expandable prosthetic heart valves can be expanded to various diameters. Mechanically expandable prosthetic heart valves can also be compressed after an initial expansion (e.g., for repositioning and/or retrieval).

Despite the recent advancements in percutaneous valve technology, there remains a need for improved transcatheter heart valves and delivery devices for such valves.

SUMMARY

Embodiments of improved prosthetic implant delivery assemblies and frames therefor are disclosed herein, as well as related methods and devices for such assemblies. In several embodiments, the disclosed assemblies are configured for delivering replacement heart valves into a heart of a patient.

In a representative embodiment, an implantable prosthetic device can comprise a frame movable between a radially compressed and a radially expanded configuration, the frame comprising an inflow end portion and an outflow end portion, the frame comprising a plurality of struts, and at least one expansion and locking mechanism. The at least one expansion and locking mechanism can comprise a first member coupled to the frame at a first location, a second member coupled to the frame at a second location spaced apart from the first location, the second member extending at least partially into the first member, and a third member having a first end portion and a second end portion, the first end portion extending at least partially into the first member and the second end portion comprising an engagement portion. The plurality of struts can include a first strut and a second strut pivotably coupled to one another to form an apex, the first strut comprising a first flange and the second strut comprising a second flange. When the frame is in the expanded configuration, advancement of the third member in a distal direction positions the engagement member between the first and second flanges such that the first and second flanges engage the engagement member to resist pivoting of the first and second struts relative to one another in a first direction to resist radial compression of the frame.

In another representative embodiment, an assembly can comprise a prosthetic heart valve and a delivery apparatus. The prosthetic heart valve can comprise a frame movable between a radially compressed and a radially expanded configuration, the frame comprising an inflow end portion and an outflow end portion, the frame comprising a first strut and a second strut comprising a first flanged portion and a second flanged portion respectively, and at least one expansion and locking mechanism. The at least one expansion and locking mechanism can comprise a first member coupled to the frame at a first location, a second member coupled to the frame at a second location spaced apart from the first location, the second member extending at least partially into the first member, and a third member comprising an engagement portion. The delivery apparatus can comprise a handle, a first actuation member extending from the handle and coupled to the first member, the first actuation member configured to apply a distally directed force to the first member, a second actuation member extending from the handle and coupled to the second member, the second actuation member configured to apply a proximally directed force to the second member, and a third actuation member extending from the handle and coupled to the third member. The prosthetic heart valve can be radially expandable from the radially compressed configuration to the radially expanded configuration upon application of at least one of the first distally directed force and the proximally directed force to the prosthetic heart valve via the first and second actuation members, respectively. When the prosthetic heart valve is in the radially expanded configuration the engagement portion of the third member selectively engages the first and second flanges to prevent compression of the frame.

In a representative embodiment, a method can comprise inserting a distal end of a delivery apparatus into the vasculature of a patient, the delivery apparatus releasably coupled to a prosthetic heart valve movable between a radially compressed and a radially expanded configuration. The prosthetic valve can comprise a frame comprising an inflow end portion, an outflow end portion, and a plurality of struts, and an expansion and locking mechanism comprising a first member coupled to the frame at a first location, a second member coupled to the frame at a second location spaced apart from the first location, and a third member having a first end portion and a second end portion comprising an engagement portion. The method can further comprise advancing the prosthetic valve to a selected implantation site, moving at least one of the first member distally and the second member proximally to radially expand the prosthetic valve, and advancing the third member distally such that the engagement portion engages one or more flanges radially extending from respective struts of the plurality of struts to lock the prosthetic valve in an expanded configuration.

In another representative embodiment, an implantable prosthetic device can comprise a frame movable between a radially compressed and a radially expanded configuration, the frame comprising an inflow end portion, an outflow end portion, and a plurality of struts including a first strut and a second strut pivotably coupled to one another to form an apex, the first strut comprising a first flange and the second strut comprising a second flange. The frame further can further comprise one or more expansion and locking mechanisms comprising a first member coupled to the frame at a first location, a second member coupled to the frame at a second location, the second member extending at least partially into the first member, and a third member extending at least partially into the second member and comprising an engagement portion. The second member can comprise a biasing member configured to bias the engagement portion of the third member toward the inflow end of the frame. When the frame is in the expanded configuration advancement of the third member in a distal direction via the biasing member positions the engagement member between the first and second flanges such that the first and second flanges engage the engagement member to resist pivoting of the first and second struts relative to one another in a first direction to resist radial compression of the frame.

In still another representative embodiment, an assembly can comprise a prosthetic heart valve and a delivery apparatus. The prosthetic heart valve can comprise a frame movable between a radially compressed and a radially expanded configuration, the frame comprising an inflow end portion, an outflow end portion, and a first strut and a second strut comprising a first flanged portion and a second flanged portion respectively. The frame can further comprise an expansion and locking mechanism comprising a first member, a second member, and a third member. The first member can be coupled to the frame at a first location, the second member can be coupled to the frame at a second location spaced apart from the first location and can comprise a biasing member configured to bias an engagement portion of the third member toward the inflow end of the frame. The delivery apparatus can comprise a handle, a first actuation member extending from the handle and coupled to the first member, the first actuation member configured to apply a distally directed force to the first member, and a second actuation member extending from the handle and coupled to the second member, the second actuation member configured to apply a proximally directed force to the second member. The prosthetic heart valve is radially expandable from the radially compressed configuration to the radially expanded configuration upon application of at least one of the first distally directed force and the proximally directed force to the prosthetic heart valve via the first and second actuation members, respectively. When the prosthetic heart valve is in the expanded configuration, advancement of the third member in a distal direction via the biasing member positions the engagement member between the first and second flanged portions such that the first and second flanged portions engage the engagement member to resist pivoting of the first and second struts relative to one another in a first direction to resist radial compression of the frame The foregoing and other objects, features, and advantages of the disclosure will become more apparent from the following detailed description, which proceeds with reference to the accompanying figures.

DETAILED DESCRIPTION

Described herein are examples of prosthetic implant delivery assemblies and components thereof which can improve a physician's ability to control the size of a mechanically-expandable prosthetic implant, such as prosthetic valves (e.g., prosthetic heart valves or venous valves), stents, or grafts, as well as facilitate separation of the prosthetic implant from the delivery assembly, during the implantation procedure. The present disclosure also provides frames for use with such prosthetic implants. The frames can comprise expansion and locking mechanisms configured to expand and/or compress the frame and to hold the frame in an expanded configuration when the implant is expanded at a selected delivery site within a patient.

Prosthetic valves disclosed herein can be radially compressible and expandable between a radially compressed state and a radially expanded state. Thus, the prosthetic valves can be crimped on or retained by an implant delivery apparatus in the radially compressed state during delivery, and then expanded to the radially expanded state once the prosthetic valve reaches the implantation site. It is understood that the valves disclosed herein may be used with a variety of implant delivery apparatuses, and examples thereof will be discussed in more detail later.

Figure 1:
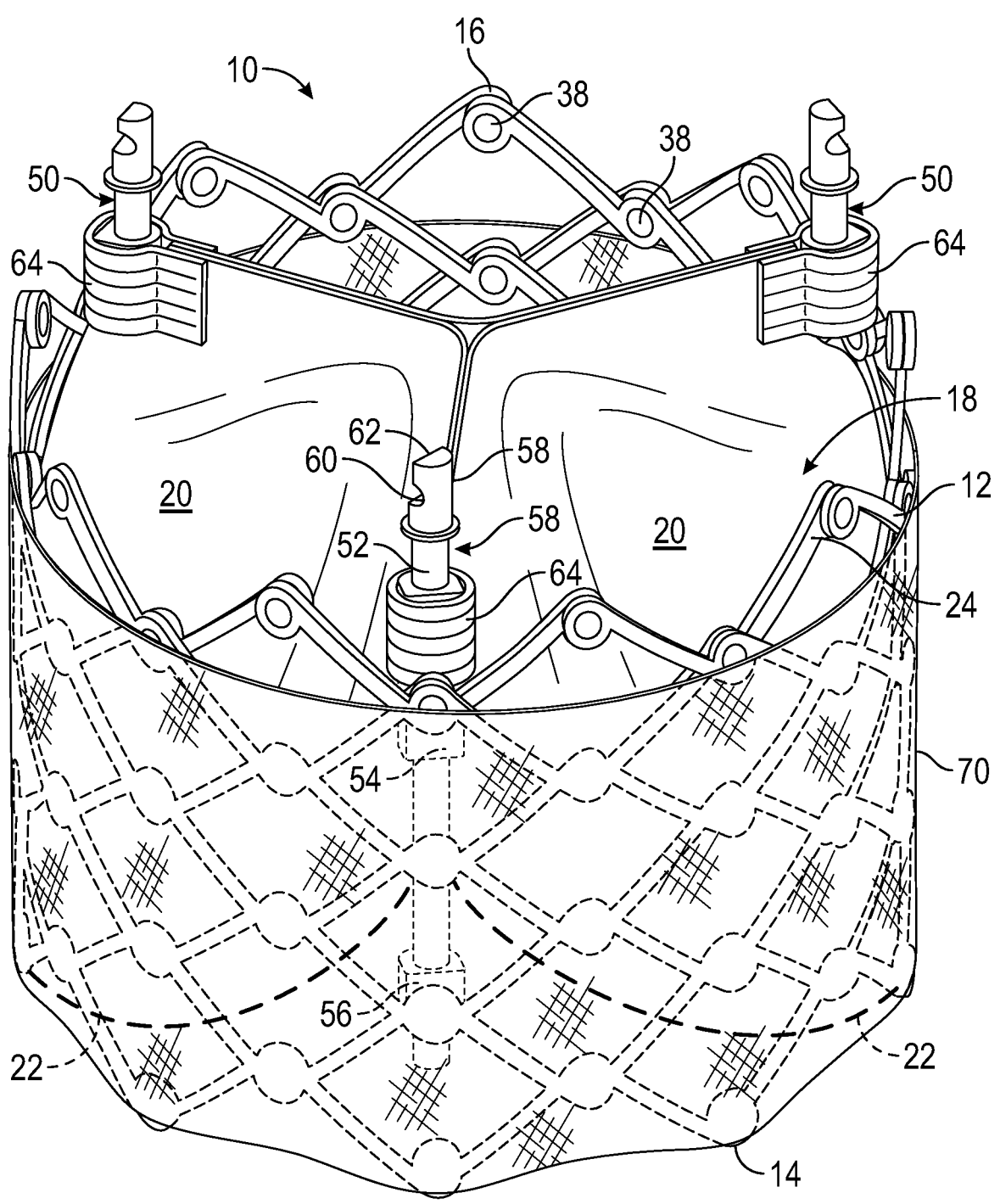
FIG. 1 is a perspective view of a prosthetic heart valve, according to one embodiment.

FIG. 1 shows an exemplary prosthetic valve 10, according to one embodiment. The prosthetic valve 10 can include an annular stent or frame 12 having an inflow end 14 and an outflow end 16. The prosthetic valve 10 can also include a valvular structure 18 which is coupled to and supported inside of the frame 12. The valvular structure 18 is configured to regulate the flow of blood through the prosthetic valve 10 from the inflow end 14 to the outflow end 16.

The valvular structure 18 can include, for example, a leaflet assembly comprising one or more leaflets 20 made of a flexible material. The leaflets 20 can be made from in whole or part, biological material, bio-compatible synthetic materials, or other such materials. Suitable biological material can include, for example, bovine pericardium (or pericardium from other sources). The leaflets 20 can be secured to one another at their adjacent sides to form commissures, each of which can be secured to a respective actuator 50 or the frame 102.

In the depicted embodiment, the valvular structure 18 comprises three leaflets 20, which can be arranged to collapse in a tricuspid arrangement. Each leaflet 20 can have an inflow edge portion 22. As shown in FIG. 1, the inflow edge portions 22 of the leaflets 20 can define an undulating, curved scallop shape that follows or tracks a plurality of interconnected strut segments of the frame 12 in a circumferential direction when the frame 12 is in the radially expanded configuration. The inflow edges of the leaflets can be referred to as a "scallop line."

In some embodiments, the inflow edge portions 22 of the leaflets 20 can be sutured to adjacent struts of the frame generally along the scallop line. In other embodiments, the inflow edge portions 22 of the leaflets 20 can be sutured to an inner skirt, which in turn in sutured to adjacent struts of the frame. By forming the leaflets 20 with this scallop geometry, stresses on the leaflets 20 are reduced, which in turn improves durability of the valve 10. Moreover, by virtue of the scallop shape, folds and ripples at the belly of each leaflet 20 (the central region of each leaflet), which can cause early calcification in those areas, can be eliminated or at least minimized. The scallop geometry also reduces the amount of tissue material used to form valvular structure 18, thereby allowing a smaller, more even crimped profile at the inflow end 14 of the valve 10.

Further details regarding transcatheter prosthetic heart valves, including the manner in which the valvular structure can be mounted to the frame of the prosthetic valve can be found, for example, in U.S. Pat. Nos. 6,730,118, 7,393,360, 7,510,575, 7,993,394, and 8,252,202, U.S. Publication No. 2018/0325665 and U.S. patent application Ser. No. 16/941, 776, filed Jul. 29, 2020, all of which are incorporated herein by reference in their entireties.

Figure 2B:
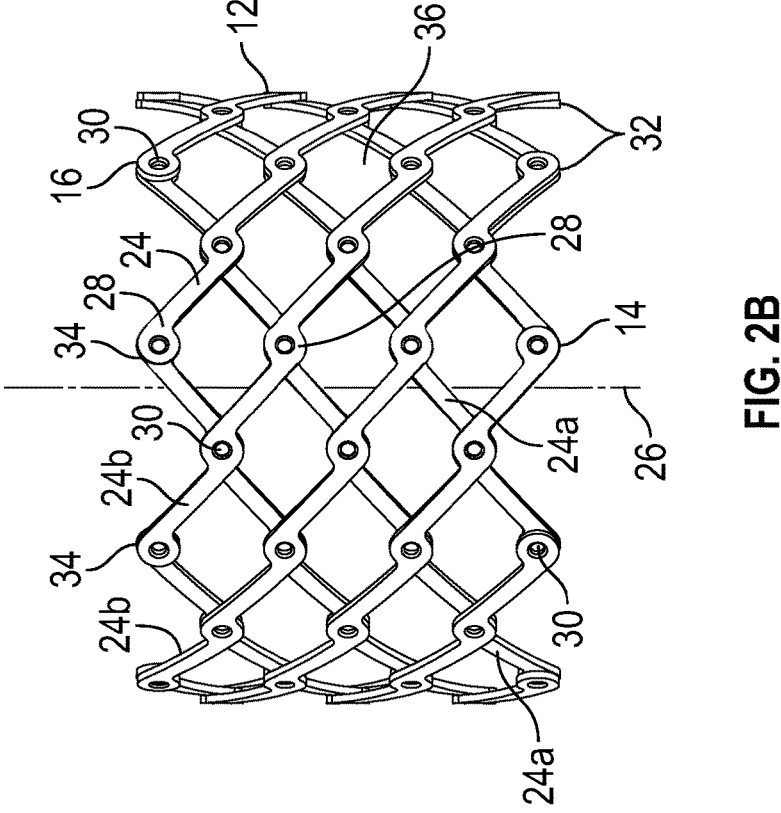
FIG. 2B is a side elevation view of the frame of the prosthetic heart valve of FIG. 1, shown in a radially expanded state.
Figure 2A:
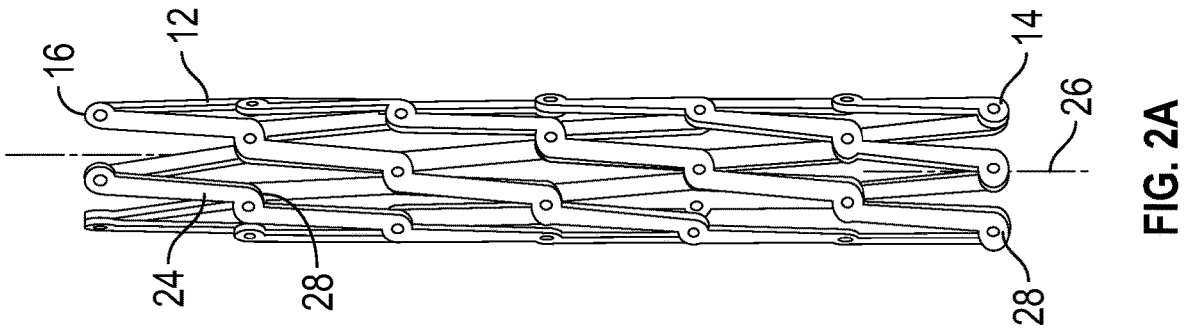
FIG. 2A is a side elevation view of the frame of the prosthetic heart valve of FIG. 1, shown in a radially compressed state.

The prosthetic valve 10 can be radially compressible and expandable between a radially compressed configuration and a radially expanded configuration. FIGS. 2A-2B show the bare frame 12 of the prosthetic valve 10 (without the leaflets and other components) for purposes of illustrating expansion of the prosthetic valve 10 from the radially compressed configuration (FIG. 2A) to the radially expanded configuration (FIG. 2B).

The frame 12 can include a plurality of interconnected lattice struts 24 arranged in a lattice-type pattern and forming a plurality of apices 34 at the outflow end 16 of the prosthetic valve 10. The struts 24 can also form similar apices 32 at the inflow end 14 of the prosthetic valve 10. In FIG. 2B, the struts 24 are shown as positioned diagonally, or offset at an angle relative to, and radially offset from, a longitudinal axis 26 of the prosthetic valve 10 when the prosthetic valve 10 is in the expanded configuration. In other implementations, the struts 24 can be offset by a different amount than depicted in FIG. 2B, or some or all of the struts 24 can be positioned parallel to the longitudinal axis 26 of the prosthetic valve 10.

The struts 24 can comprise a set of inner struts 24a (extending from the lower left to the upper right of the frame in FIG. 2B) and a set of outer struts 24b (extending from the upper left to the lower right of the frame in FIG. 2B) connected to the inner struts 24a. The open lattice structure of the frame 12 can define a plurality of open frame cells 36 between the struts 24.

The struts 24 can be pivotably coupled to one another at one or more pivot joints or pivot junctions 28 along the length of each strut. For example, in one embodiment, each of the struts 24 can be formed with apertures 30 at opposing ends of the strut and apertures spaced along the length of the strut. Respective hinges can be formed at the locations where struts 24 overlap each other via fasteners 38 (FIG. 1), such as rivets or pins that extend through the apertures 30. The hinges can allow the struts 24 to pivot relative to one another as the frame 12 is radially expanded or compressed, such as during assembly, preparation, or implantation of the prosthetic valve 10.

The frame struts and the components used to form the pivot joints of the frame 12 (or any frames described below) can be made of any of various suitable materials, such as stainless steel, a cobalt chromium alloy, or a nickel titanium alloy ("NiTi"), for example Nitinol. In some embodiments, the frame 12 can be constructed by forming individual components (e.g., the struts and fasteners of the frame) and then mechanically assembling and connecting the individual components together. Further details regarding the construction of the frame and the prosthetic valve are described in U.S. Pat. Nos. 10,603,165 and 10,806,573, U.S. Publication Nos. 2018/0344456 and 2020/0188099, all of which are incorporated herein by reference.

In the illustrated embodiment, the prosthetic valve 10 can be mechanically expanded from the radially contracted configuration to the radially expanded configuration. For example, the prosthetic valve 10 can be radially expanded by maintaining the inflow end 14 of the frame 12 at a fixed position while applying a force in the axial direction against the outflow end 16 toward the inflow end 14. Alternatively, the prosthetic valve 10 can be expanded by applying an axial force against the inflow end 14 while maintaining the outflow end 16 at a fixed position, or by applying opposing axial forces to the inflow and outflow ends 14, 16, respectively.

As shown in FIG. 1, the prosthetic valve 10 can include one or more actuators 50 mounted to and equally spaced around the inner surface of the frame 12. Each of the actuators 50 can be configured to form a releasable connection with one or more respective actuators of a delivery apparatus.

In the illustrated embodiment, expansion and compression forces can be applied to the frame by the actuators 50. Referring again to FIG. 1, each of the actuators 50 can comprise a screw or threaded rod 52, a first anchor in the form of a cylinder or sleeve 54, and a second anchor in the form of a threaded nut 56. The rod 52 extends through the sleeve 54 and the nut 56. The sleeve 54 can be secured to the frame 12, such as with a fastener 38 that forms a hinge at the junction between two struts. Each actuator 50 is configured to increase the distance between the attachment locations of a respective sleeve 54 and nut 56, which causes the frame 12 to elongate axially and compress radially, and to decrease the distance between the attachment locations of a respective sleeve 54 and nut 56, which causes the frame 12 to fore-shorten axially and expand radially.

For example, each rod 52 can have external threads that engage internal threads of the nut 56 such that rotation of the rod causes corresponding axial movement of the nut 56 toward or away from the sleeve 54 (depending on the direction of rotation of the rod 52). This causes the hinges supporting the sleeve 54 and the nut 56 to move closer towards each other to radially expand the frame or to move farther away from each other to radially compress the frame, depending on the direction of rotation of the rod 52.

In other embodiments, the actuators 50 can be reciprocating type actuators configured to apply axial directed forces to the frame to produce radial expansion and compression of the frame. For example, the rod 52 of each actuator can be fixed axially relative to the sleeve 56 and slidable relative to the sleeve 54. Thus, in this manner, moving the rod 52 distally relative to the sleeve 54 and/or moving the sleeve 54 proximally relative to the rod 52 radially compresses the frame. Conversely, moving the rod 52 proximally relative to the sleeve 54 and/or moving the sleeve 54 distally relative to the rod 52 radially expands the frame.

When reciprocating type actuators are used, the prosthetic valve can also include one or more locking mechanisms that retain the frame in the expanded state. The locking mechanisms can be separate components that are mounted on the frame apart from the actuators, or they can be a sub-component of the actuators themselves.

Each rod 52 can include an attachment member 58 along a proximal end portion of the rod 52 configured to form a releasable connection with a corresponding actuator of a delivery apparatus. The actuator(s) of the delivery apparatus can apply forces to the rods for radially compressing or expanding the prosthetic valve 10. The attachment member 58 in the illustrated configuration comprises a notch 60 and a projection 62 that can engage a corresponding projection of an actuator of the delivery apparatus.

In the illustrated embodiments, the prosthetic valve 10 includes three such actuators 50, although a greater or fewer number of actuators could be used in other embodiments. The leaflets 20 can have commissure attachments members 64 that wrap around the sleeves 54 of the actuators 50. Further details of the actuators, locking mechanisms and delivery apparatuses for actuating the actuators can be found in U.S. Pat. No. 10,603,165 and U.S. Publication Nos. 2019/0060057, and 2018/0325665, each of which is incorporated herein by reference in its entirety. Any of the actuators and locking mechanisms disclosed in the previously filed applications can be incorporated in any of the prosthetic valves disclosed herein. Further, any of the delivery apparatuses disclosed in the previously filed applications can be used to deliver and implant any of the prosthetic valves discloses herein.

The prosthetic valve 10 can include one or more skirts or sealing members. In some embodiments, the prosthetic valve 10 can include an inner skirt (not shown) mounted on the inner surface of the frame. The inner skirt can function as a sealing member to prevent or decrease perivalvular leakage, to anchor the leaflets to the frame, and/or to protect the leaflets against damage caused by contact with the frame during crimping and during working cycles of the prosthetic valve. As shown in FIG. 1, the prosthetic valve 10 can also include an outer skirt 70 mounted on the outer surface of the frame 12. The outer skirt 70 can function as a sealing member for the prosthetic valve by sealing against the tissue of the native valve annulus and helping to reduce paravalvular leakage past the prosthetic valve. The inner and outer skirts can be formed from any of various suitable biocompatible materials, including any of various synthetic materials, including fabrics (e.g., polyethylene terephthalate fabric) or natural tissue (e.g., pericardial tissue). Further details regarding the use of skirts or sealing members in prosthetic valve can be found, for example, in U.S. Pat. No. 10,806, 573, which is incorporated herein by reference in its entirety.

Figures 3, 4:
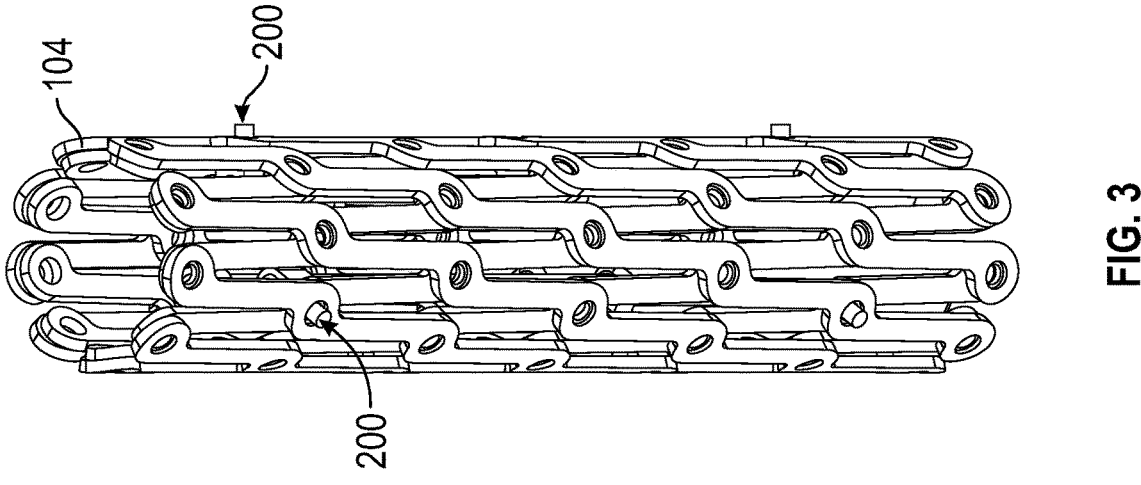
FIG. 3 is a perspective view of a prosthetic valve frame, shown in a radially collapsed state, having a plurality of expansion and locking mechanisms, according to another embodiment.
FIG. 4 is a perspective view of the frame and the expansion and locking mechanisms of FIG. 3, with the frame shown in a radially expanded state.

FIGS. 3-4 show another embodiment of a prosthetic valve 100 comprising a frame 104 and expansion and locking mechanisms 200 (also referred to as "actuators"). It should be understood that the prosthetic valve 100 can include leaflets 20 and other soft components, such as one or more skirts 70, which are removed for purposes of illustration. Expansion and locking mechanism 200 can be used to both radially expand and lock the prosthetic valve in a radially expanded state. In the example of FIGS. 3 and 4, three expansion and locking mechanisms 200 are attached to the frame 104 but in other example delivery assemblies, any number of expansion and locking mechanisms 200 can be used. FIG. 3 shows the expansion and locking mechanisms 200 attached to the frame 104 when the frame is in a radially collapsed configuration and FIG. 4 shows expansion and locking mechanisms attached to the frame when the frame is in a radially expanded configuration.

It will be appreciated that prosthetic valve 100 can, in certain embodiments, use other mechanisms for expansion and locking, such as linear actuators, alternate locking mechanisms, and alternate expansion and locking mechanisms. Further details regarding the use of linear actuators, locking mechanisms, and expansion and locking mechanisms in prosthetic valve can be found, for example, in U.S. Pat. No. 10,603,165.

Figures 5A, 5B, 5C:
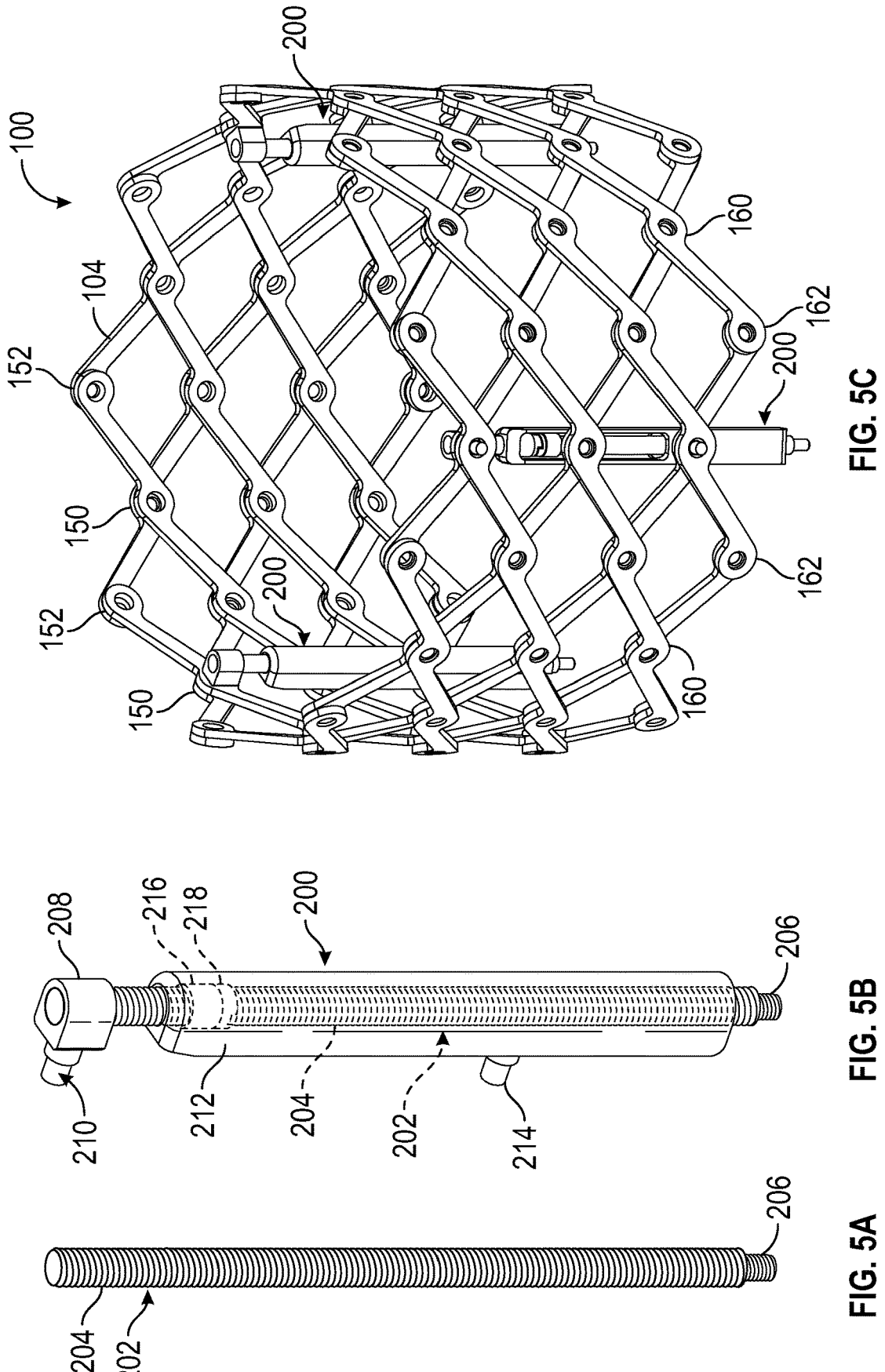
FIG. 5A is a perspective view of a screw of one of the expansion and locking mechanisms of FIG. 3.
FIG. 5B is a perspective view of one of the expansion and locking mechanisms of FIG. 3.
FIG. 5C is another perspective view of the frame and the expansion and locking mechanisms of FIG. 3, with the frame shown in a radially expanded state.

Referring to FIGS. 5A-5C, the expansion and locking mechanism 200 in the illustrated embodiment can include an actuator screw 202 (which functions as a linear actuator or a push-pull member in the illustrated embodiment) comprising a relatively long upper, or distal, portion 204 and a relatively shorter lower, or proximal, portion 206 at the proximal end of the screw 200, wherein the lower portion has a smaller diameter than the upper portion. Both the upper and lower portions 204, 206 of the screw 202 can have externally threaded surfaces.

The actuator screw 200 can have a distal attachment piece 208 attached to its distal end having a radially extending distal valve connector 210. The distal attachment piece 208 can be fixed to the screw 202 (e.g., welded together or manufactured as one piece). The distal valve connector 210 can extend through an opening at or near the distal end of the frame 104 formed at a location on the frame where two or more struts intersect as shown in FIG. 5C. The distal valve connector 210 can be fixed to the frame 104 (e.g., welded). Due to the shape of the struts, the distal end of the frame 104 comprises an alternating series of distal junctions 150 and distal apices 152. In the illustrated example, the distal valve connectors 210 of the three expansion and locking mechanisms 200 are connected to the frame 104 through distal junctions 150. In other examples, one or more distal valve connectors 210 can be connected to the frame 104 through distal apices 152. In other embodiments, the distal valve connectors 210 can be connected to junctions closer to the proximal end of the frame 104.

The expansion and locking mechanism 200 can further include a sleeve 212. The sleeve 212 can be positioned annularly around the distal portion 204 of the screw 202 and can contain axial openings at its proximal and distal ends through which the screw 202 can extend. The axial openings and the lumen in the sleeve 212 can have a diameter larger than the diameter of the distal portion 204 of the screw 202 such that the screw can move freely within the sleeve (the screw 202 can be moved proximally and distally relative to the sleeve 212). Because the actuator screw 202 can move freely within the sleeve, it can be used to radially expand and/or contract the frame 104 as disclosed in further detail below.

The sleeve 212 can have a proximal valve connector 214 extending radially from its outer surface. The proximal valve connector 214 can be fixed to the sleeve 212 (e.g., welded). The proximal valve connector 214 can be axially spaced from the distal valve connector 210 such that the proximal valve connector can extend through an opening at or near the proximal end of the frame 104. The proximal end of the frame 104 comprises an alternating series of proximal junctions 160 and proximal apices 162. In the illustrated example, the proximal valve connectors 214 of the three expansion and locking mechanisms 200 are connected to the frame 104 through proximal junctions 160. In other examples, one or more proximal valve connectors 214 can be connected to the frame 104 through proximal apices 162. In other embodiments, the proximal valve connectors 214 can be connected to junctions closer to the distal end of the frame 104.

It should be understood that the distal and proximal connectors 210, 214 need not be connected to opposite ends of the frame. The actuator 200 can be used to expand and compress the frame as long as the distal and proximal connectors are connected to respective junctions on the frame that are axially spaced from each other.

A locking nut 216 can be positioned inside of the sleeve 212 and can have an internally threaded surface that can engage the externally threaded surface of the actuator screw 202. The locking nut 216 can have a notched portion 218 at its proximal end, the purpose of which is described below. The locking nut can be used to lock the frame 104 into a particularly radially expanded state, as discussed below.

Figure 6:
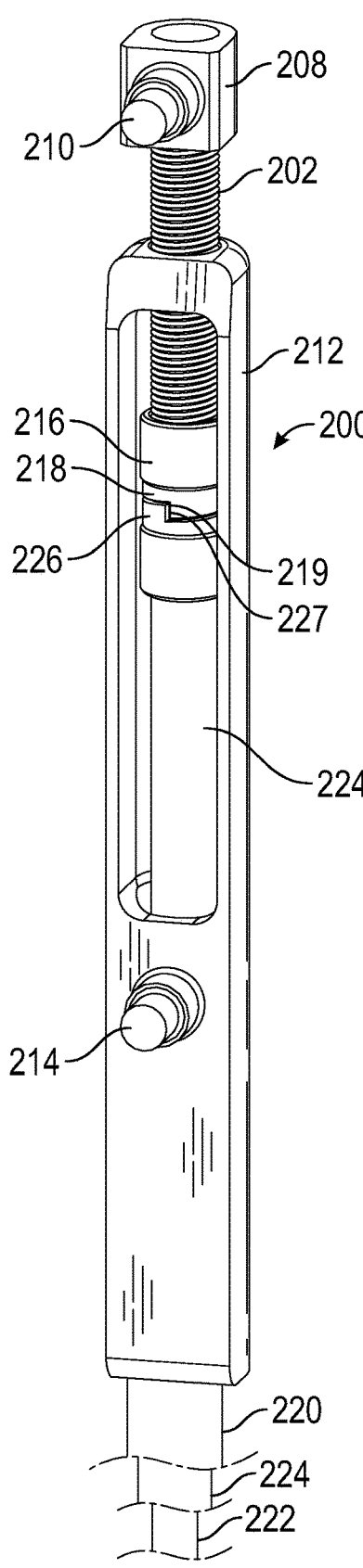
FIG. 6 is another perspective view of one of the expansion and locking mechanisms of FIG. 3.
Figure 7:
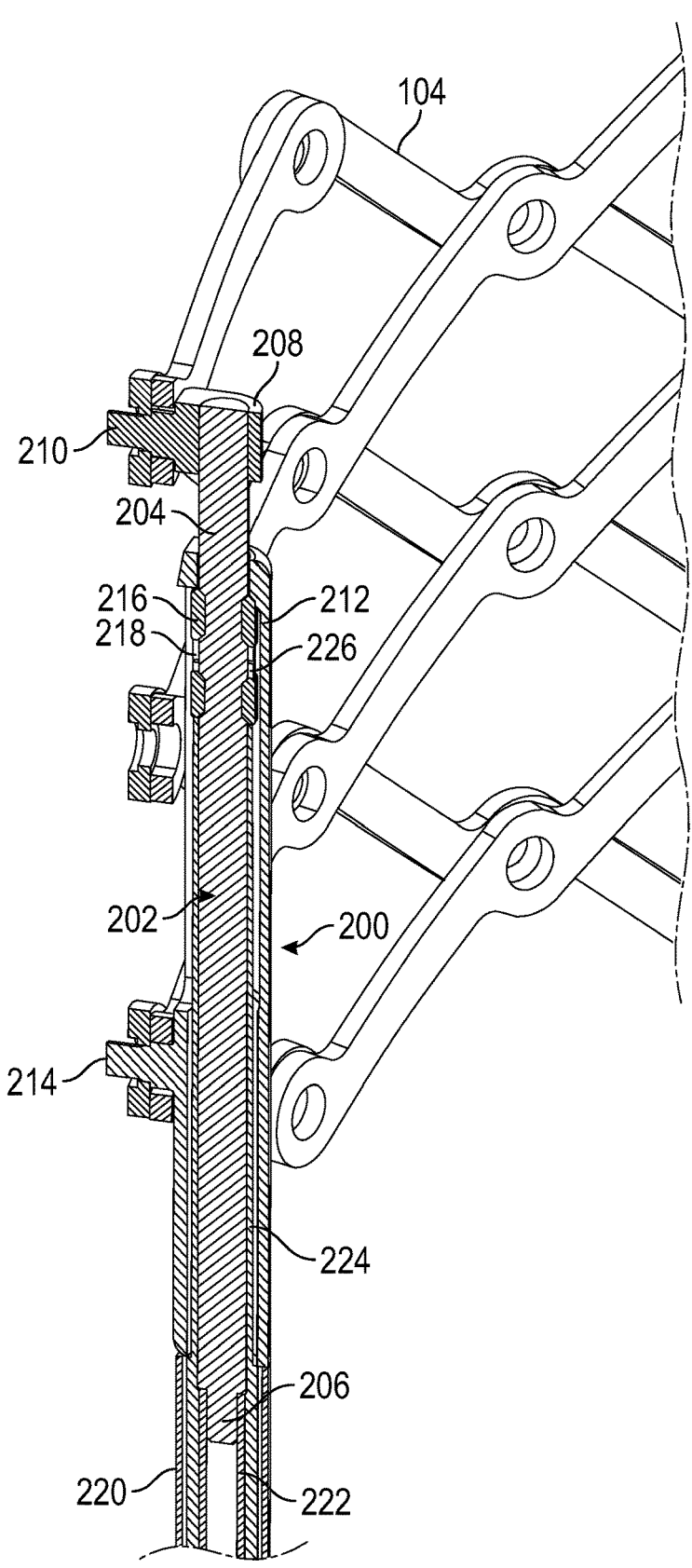
FIG. 7 show s a cross sectional view of one of the expansion and locking mechanisms of FIG. 3 along with a portion of the frame.

FIGS. 6 and 7 shows the expansion and locking mechanism 200 including components of a delivery apparatus not shown in FIGS. 5A-5C. As shown, the expansion and locking mechanism 200 can be releasably coupled to a support tube 220, an actuator member 222, and a locking tool 224. The proximal end of the support tube 220 can be connected to a handle or other control device (not shown) that a doctor or operator of the delivery assembly utilizes to operate the expansion and locking mechanism 200 as described herein. Similarly, the proximal ends of the actuator member 222 and the locking tool 224 can be connected to the handle.

The support tube 220 annularly surrounds a proximal portion of the locking tool 224 such that the locking tool extends through a lumen of the support tube. The support tube 220 and the sleeve are sized such that the distal end of the support tube abuts or engages the proximal end of the sleeve 212 such that the support tube is prevented from moving distally beyond the sleeve.

The actuator member 222 extends through a lumen of the locking tool 224. The actuator member 222 can be, for example, a shaft, a rod, a cable, or wire. The distal end portion of the actuator member 222 can be releasably connected to the proximal end portion 206 of the actuator screw 202. For example, the distal end portion of the actuator member 222 can have an internally threaded surface that can engage the external threads of the proximal end portion 206 of the actuator screw 202. Alternatively, the actuator member 222 can have external threads that engage an internally threaded portion of the screw 202. When the actuator member 222 is threaded onto the actuator screw 202, axial movement of the actuator member causes axial movement of the screw.

The distal portion of the locking tool 224 annularly surrounds the actuator screw 202 and extends through a lumen of the sleeve 212 and the proximal portion of the locking tool annularly surrounds the actuator member 222 and extends through a lumen of the support tube 220 to the handle of the delivery device. The locking tool 224 can have an internally threaded surface that can engage the externally threaded surface of the locking screw 202 such that clockwise or counter-clockwise rotation of the locking tool 224 causes the locking tool to advance distally or proximally along the screw, respectively.

The distal end of the locking tool 224 can comprise a notched portion 226, as can best be seen in FIG. 6. The notched portion 226 of the locking tool 224 can have an engagement surface 227 that is configured to engage a correspondingly shaped engagement surface 219 of the notched portion 218 of the locking nut 216 such that rotation of the locking tool (e.g., clockwise rotation) causes the nut 216 to rotate in the same direction (e.g., clockwise) and advance distally along the locking screw 202. The notched portions 218, 226 in the illustrated embodiment are configured such that rotation of the locking tool 224 in the opposite direction (e.g., counter-clockwise) allows the notched portion 226 of the tool 224 to disengage the notched portion 218 of the locking nut 216; that is, rotation of the locking tool in a direction that causes the locking tool to move proximally does not cause corresponding rotation of the nut.

In alternative embodiments, the distal end portion of the locking tool 224 can have various other configurations adapted to engage the nut 216 and produce rotation of the nut upon rotation of the locking tool for moving the nut distally, such as any of the tool configurations described herein. In some embodiments, the distal end portion of the locking tool 224 can be adapted to produce rotation of the nut 216 in both directions so as move the nut distally and proximally along the locking screw 202.

In operation, prior to implantation, the actuator member 222 is screwed onto the proximal end portion 206 of the actuator screw 202 and the locking nut 216 is rotated such that it is positioned at the proximal end of the screw. The frame 104 can then be placed in a radially collapsed state and the delivery assembly can be inserted into a patient. Once the prosthetic valve is at a desired implantation site, the frame 104 can be radially expanded as described herein.

To radially expand the frame 104, the support tube 220 is held firmly against the sleeve 212. The actuator member 222 is then pulled in a proximal direction through the support tube, such as by pulling on the proximal end of the actuator member or actuating a control knob on the handle that produces proximal movement of the actuator member. Because the support tube 220 is being held against the sleeve 212, which is connected to a proximal end of the frame 104 by the proximal valve connector 214, the proximal end of the frame is prevented from moving relative to the support tube. As such, movement of the actuator member 222 in a proximal direction causes movement of the actuator screw 202 in a proximal direction (because the actuator member is threaded onto the screw), thereby causing the frame 104 to foreshorten axially and expand radially. Alternatively, the frame 104 can be expanded by moving the support tube 220 distally while holding the actuator member 222 stationary or moving the support tube distally while moving the actuator member 222 proximally.

After the frame 104 is expanded to a desired radially expanded size, the frame can be locked at this radially expanded size as described herein. Locking the frame can be achieved by rotating the locking tool 224 in a clockwise direction causing the notched portion 226 of the locking tool to engage the notched portion 218 of the locking nut 216, thereby advancing the locking nut distally along the actuator screw 202. The locking tool 224 can be so rotated until the locking nut 216 abuts an internal shoulder at the distal end of the sleeve 212 and the locking nut 216 cannot advance distally any further (see FIG. 6). This will prevent the screw 202 from advancing distally relative to the sleeve 212 and radially compressing the frame 104. However, in the illustrated embodiment, the nut 216 and the screw 202 can still move proximally through the sleeve 212, thereby allowing additional expansion of the frame 104 either during implantation or later during a valve-in-valve procedure.

Once the frame 104 is locked in radially expanded state, the locking tool 224 can be rotated in a direction to move the locking tool proximally (e.g., in a counter-clockwise direction) to decouple the notched portion 226 from the notched portion 218 of the locking nut 216 and to unscrew the locking tool from the actuator screw 204. Additionally, the actuator member 222 can be rotated in a direction to unscrew the actuator member from the lower portion 206 of the actuator screw 202 (e.g., the actuator member 222 can be configured to disengage from the actuator screw when rotated counter-clockwise). Once the locking tool 224 and the actuator member 222 are unscrewed from the actuator screw 204, they can be removed from the patient along with the support tube 220, leaving the actuator screw and the sleeve 212 connected to the frame 104, as shown in FIG. 5C, with the frame 104 locked in a particular radially-expanded state.

In an alternative embodiment, the locking tool 224 can be formed without internal threads that engage the external threads of the actuator screw 202, which can allow the locking tool 224 to be slid distally and proximally through the sleeve 212 and along the actuator screw 202 to engage and disengage the nut 216.

In some embodiments, additional designs for expansion and locking mechanisms can be used instead of the design previously described. Details on expansion and locking mechanisms can be found, for example, in U.S. Pat. No. 10,603,165.

Figures 8, 9, 10:
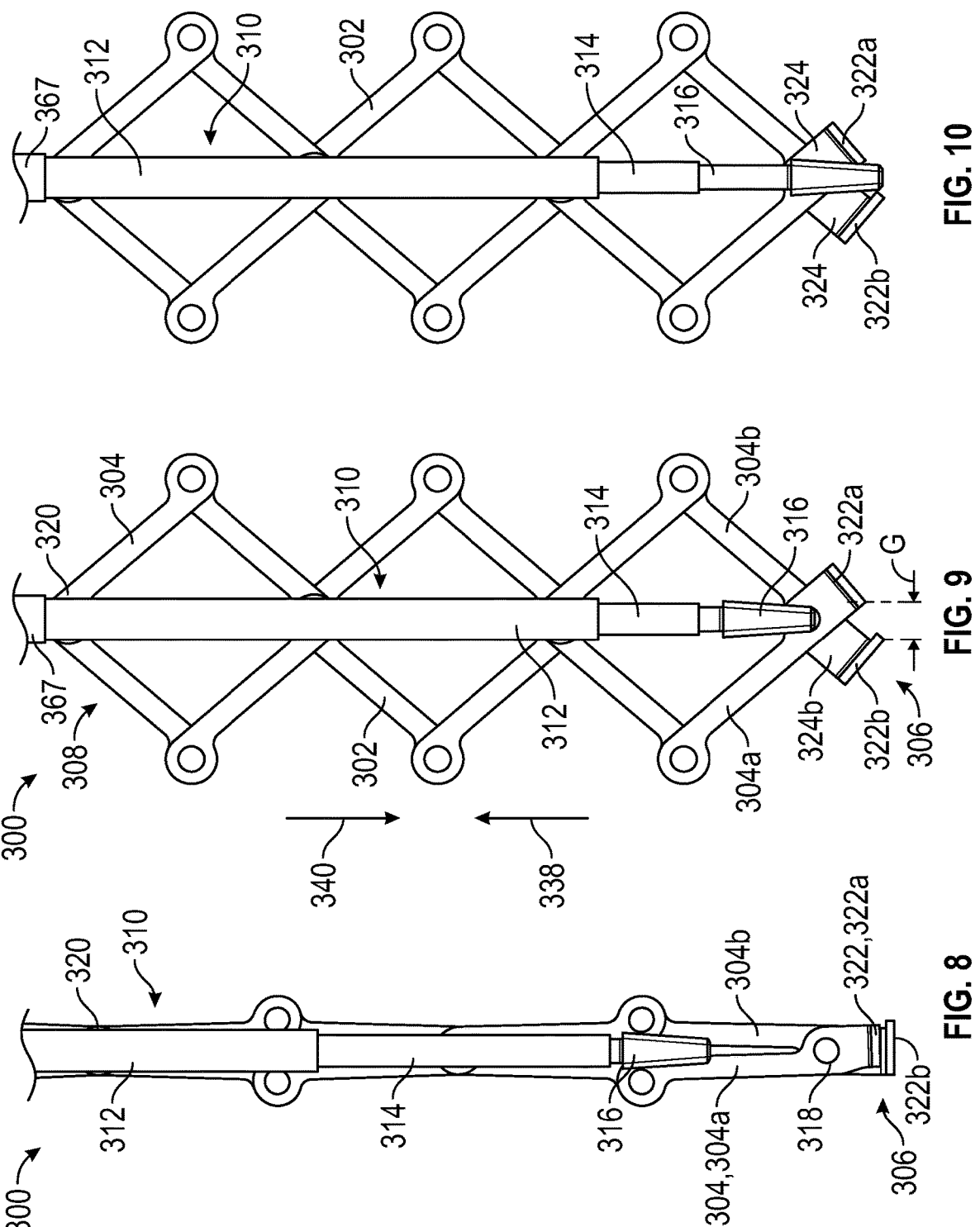
FIG. 8 is a side elevational view of a portion of a frame for a prosthetic heart valve comprising an expansion and locking mechanism, according to one embodiment.
FIG. 9 is a side elevational view of a portion of the frame of FIG. 8 shown in an expanded configuration.
FIG. 10 is a side elevational view of a portion of the frame of FIG. 8 shown in an expanded and locked configuration.

FIGS. 8-10 illustrate an exemplary embodiment of a prosthetic heart valve 300 comprising a frame 302 and one or more expansion and locking mechanisms 310. Though the described embodiments refer to a mechanically expandable prosthetic valve having pivotably coupled struts, the expansion and locking mechanisms described herein can also be used with other mechanically expandable prosthetic valves, such as those described in U.S. Provisional Application No. 63/085,947, which is incorporated herein by reference in its entirety.

The frame 302 comprises a plurality of pivotably connected struts 304 defining an inflow end 306 (which is the distal end of the frame in the delivery configuration for the illustrated embodiment) and an outflow end 308 (which is the proximal end of the frame in the delivery configuration for the illustrated embodiment). The struts 304 are pivotably connected to each other at a plurality of junctions that permit pivoting of the struts relative to each other when the frame 302 is radially compressed and expanded, as described above in connection with prosthetic valves 10 and 100.

The prosthetic valve 300 can include a valvular structure (e.g., valvular structure 18) and inner and/or outer skirts, as previously described, although these components are omitted for purposes of illustration. While only a portion of the frame 302 is depicted in FIGS. 8-10, it should be appreciated that frame 302 forms an annular structure similar to frame 12 of prosthetic valve 10. The one or more expansion and locking mechanisms 310 can be used in lieu of or in addition to actuators 50 described above, and can comprise a first or outer member 312, a second or inner member 314, and a third or locking member 316. The expansion and locking mechanisms 310 can be used to radially expand the frame 302 and to lock the frame in a radially expanded state, as described in more detail below.

The frame 302 can comprise a plurality of inflow junctions or apices 318 at the inflow end portion 306 and a plurality of outflow junctions or apices 320 at the outflow end portion 308. Selected inflow apices 318 can comprise one or more flanges 322 configured to engage the locking member 316 of the expansion and locking mechanism 310 to lock the prosthetic valve 300 in the radially expanded configuration. As shown in the illustrated embodiment, the expansion and locking mechanisms 310 can be circumferentially aligned with the selected inflow apices 318 comprising flanges 322.

For example. FIGS. 8-10 illustrate a selected inflow apex 322 comprising a first, radially inner strut 304a and a second, radially outer strut 304b. First strut 304a can include first flange 322a and second strut 304b can include second flange 322b. As the frame 302 expands, the first and second struts 304a, 304b (and therefore first and second flanges 322a. 322b), pivot relative to one another to define a gap G between them, as shown in FIG. 9. Each flange 322a, 322b can comprise a respective axial portion 324a, 324b that extends axially past the junction of the first and second struts 304a, 304b, and a respective radial portion 326a, 326b (FIG. 15) that extends radially inward toward a longitudinal axis of the prosthetic valve 300. In other embodiments, the expansion and locking mechanisms 310 can be mounted on the outside of the frame 312 and the radial portions 326a, 326b can extend radially outward from the frame.

Figures 14, 15, 16:
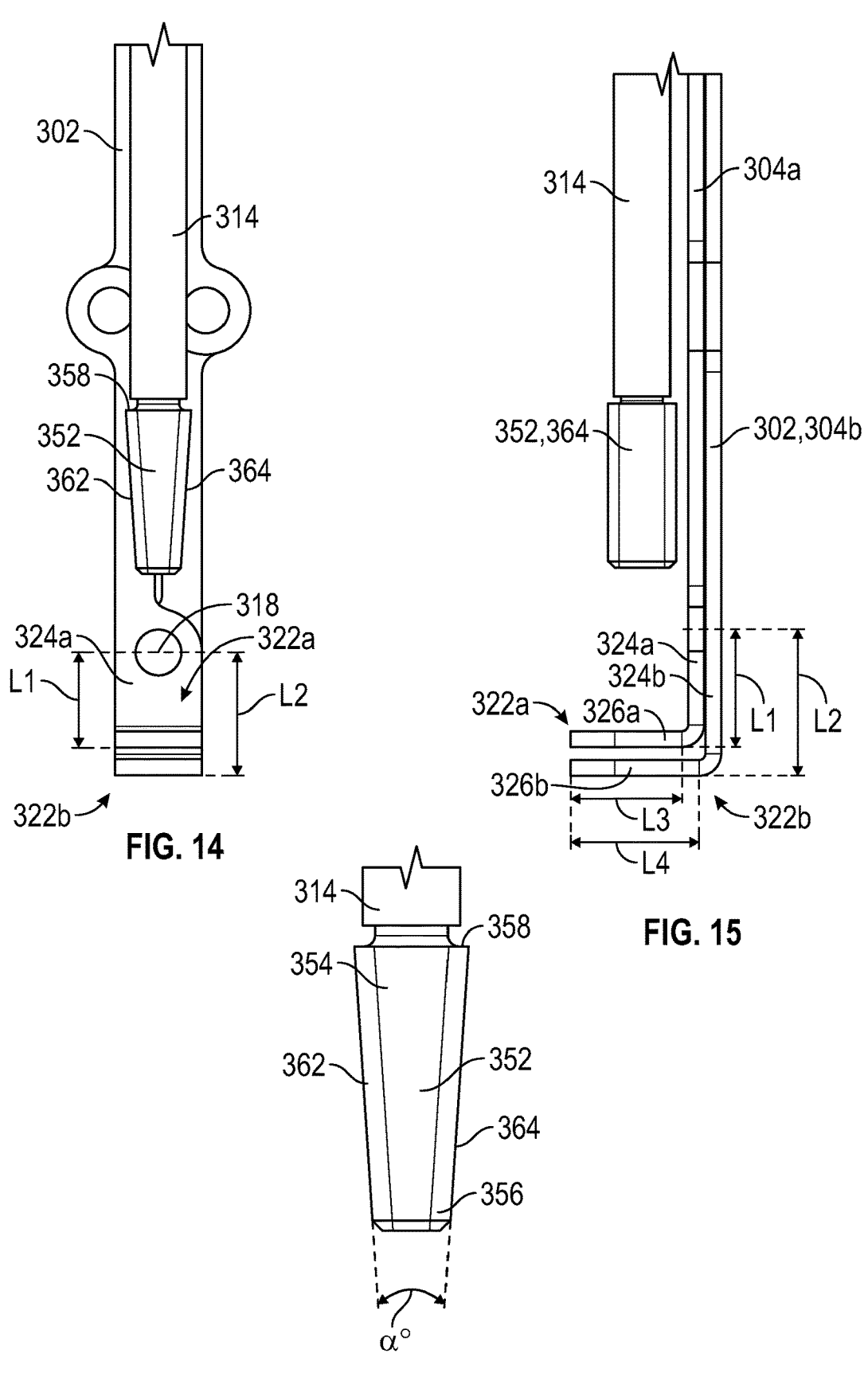
FIG. 14 is a side elevational view of a portion of the frame of FIG. 8 shown in a compressed configuration.
FIG. 15 is a side elevational view of a portion of the frame of FIG. 8 shown in a compressed configuration.
FIG. 16 is a side elevational view of a portion of the expansion and locking mechanism of FIG. 11.

As best shown in FIGS. 14-15, the first axial portion 324a can have a length $L_1$ and the second axial portion 324b can have a length $L_2$. The length $L_2$ can be greater than the length $L_1$, or vice versa, such that when the frame 302 is in the radially compressed configuration (see e.g., FIGS. 14-15) the radial portions 326a. 326b can be circumferentially aligned with one another (meaning that their respective circumferential positions are aligned along a line that is parallel to a longitudinal axis of the frame). The differing lengths $L_1$ and $L_2$ of the axial portions 324a, 324b allow the flanges 322a, 322b to pivot relative to one another about inflow apex 318 without the radial portions 326a. 326b contacting or abutting one another.

Referring now to FIG. 15, the first radial portion 326a can have a length $L_3$ and the second radial portion 326b can have a length $L_4$. Length $L_4$ can be greater than length $L_3$ such that when the radial portions 326a, 326b are circumferentially aligned with one another both radial portions terminate at substantially the same radial location. In other words, neither radial portion extends past the other. In other embodiments, such as embodiments wherein second strut 304b is positioned radially inwards of first strut 304a, the length $L_3$ can be greater than the length $L_4$.

While FIGS. 8-10 show only a single expansion and locking mechanism 310 mounted to the frame 302, it should be appreciated that the prosthetic valve 300 can comprise any number of expansion and locking mechanisms 310. For example, in some embodiments, a prosthetic valve can comprise two expansion and locking mechanisms, or three expansion and locking mechanisms, or four expansion and locking mechanisms, etc. The expansion and locking mechanisms 310 can be placed at any position about the circumference of the frame 302. For example, in some embodiments, the expansion and locking mechanisms 310 can be equally spaced from one another about the circumference of the frame 302. In other embodiments, it can be advantageous to have two or more expansion and locking mechanisms 310 situated adjacent to one another.

Figures 11, 12:
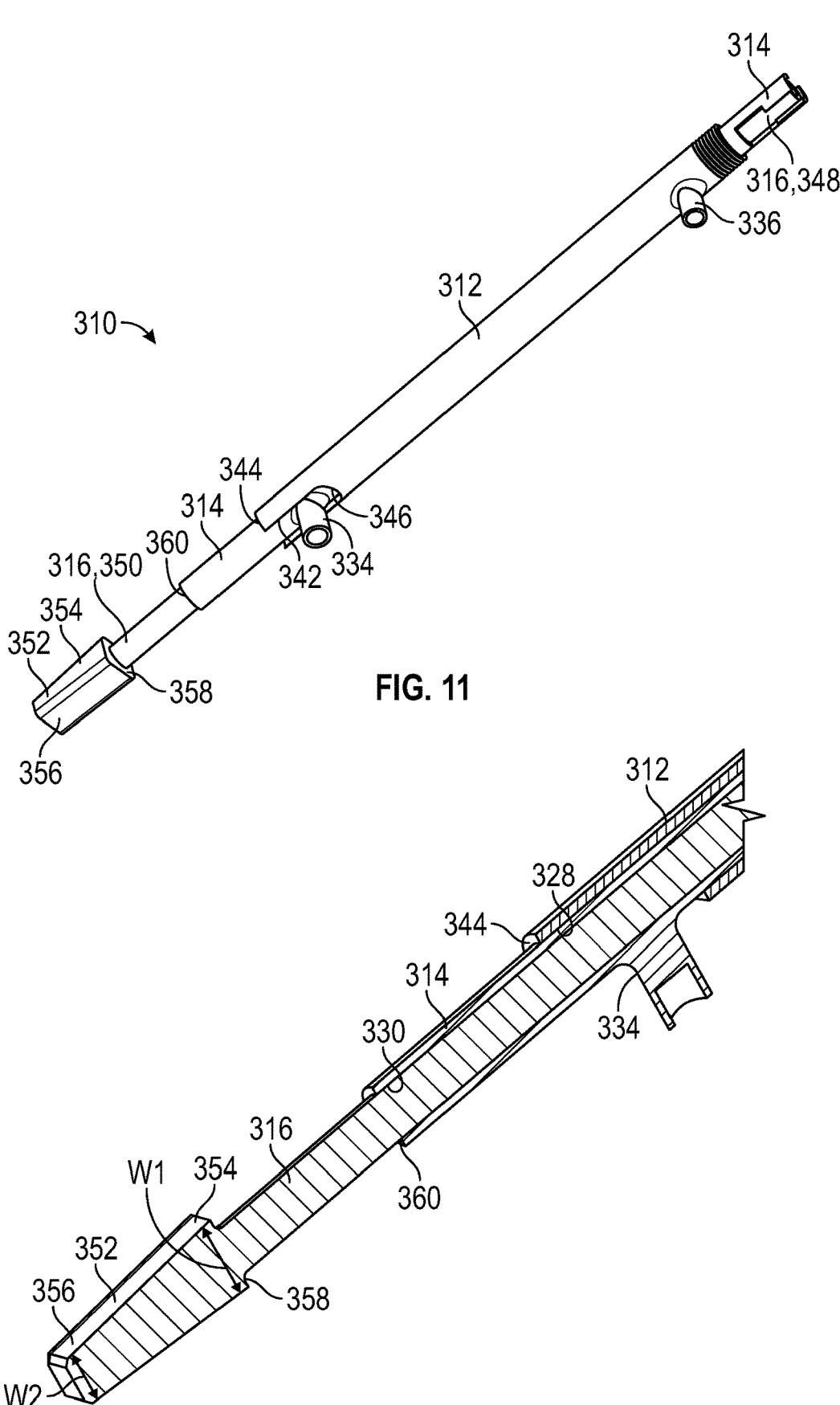
FIG. 11 is a perspective view of an expansion and locking mechanism of FIG. 8.
FIG. 12 is a cross-sectional perspective view of a portion of the expansion and locking mechanism of FIG. 11.

Referring to FIG. 11, as mentioned previously, each expansion and locking mechanism 310 can include a first, or outer member 312, a second or inner member 314, and a locking member 316. The outer member 312 can comprise a first lumen or bore 328 (FIG. 12) sized to receive at least a portion of the inner member 314, and the inner member 314 can comprise a second lumen or bore 330 (FIG. 12)

sized to receive at least a portion of the locking member 316. The outer member 312, inner member 314, and locking member 316, can each move axially relative to one another.

Figure 13:
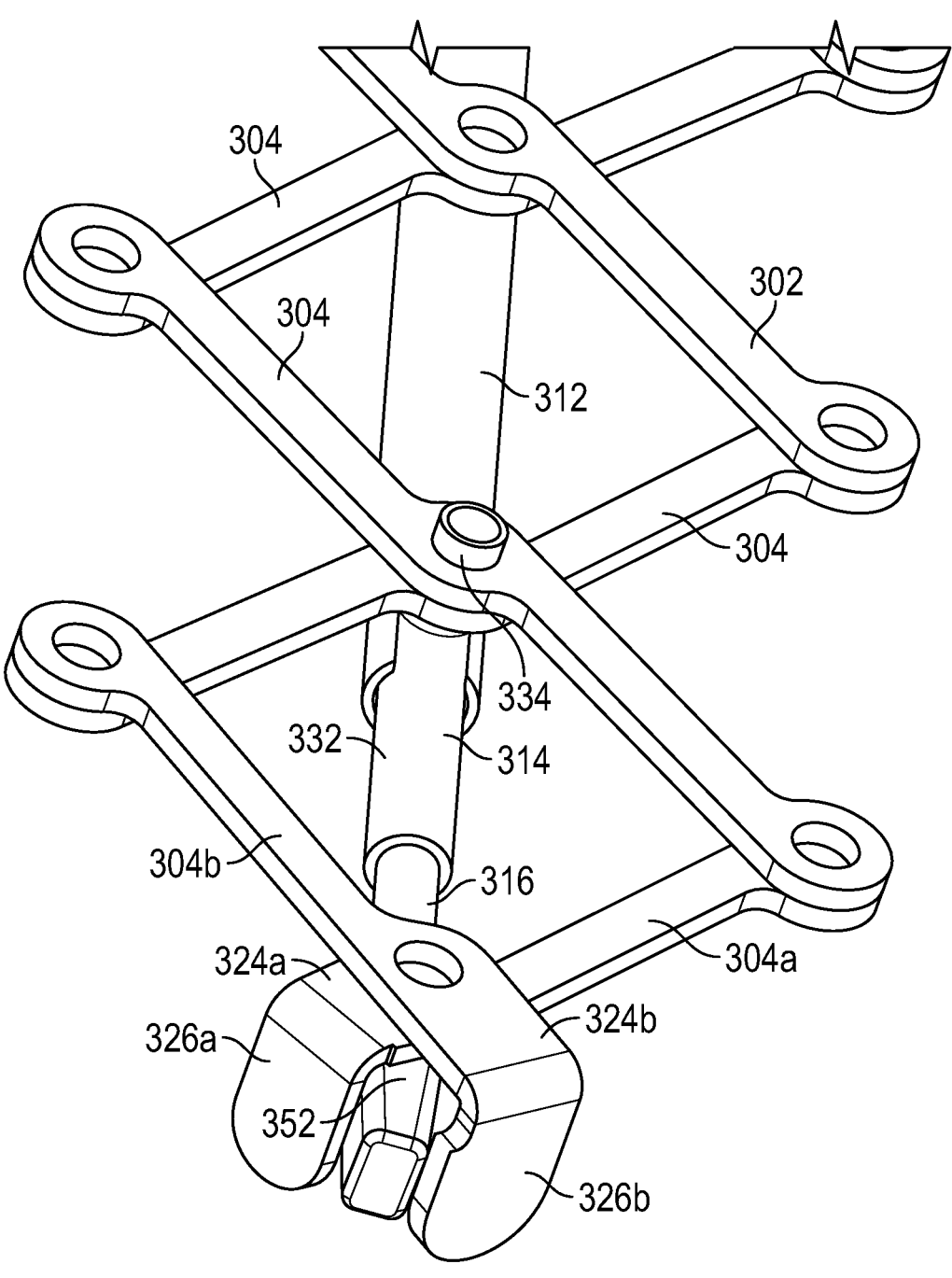
FIG. 13 is a perspective view of a portion of the frame of FIG. 8 shown in an expanded and locked configuration.

As best shown in FIG. 13, a distal end portion 332 of the inner member 314 can be coupled to the frame 302 at a first location via a fastener 334 that is affixed to and extends radially from the distal end portion 332 of the inner member 314. The fastener can be, for example, a rivet or a pin. As shown, in some embodiments, the fastener 334 can extend through corresponding apertures at a junction of two overlapping struts 304 of frame 302 and can serve as a pivot pin around which the two struts 304 can pivot relative to one another and the inner member 314. In some embodiments, an end cap or nut can be disposed over an end portion of the fastener 334 to retain the fastener within the corresponding apertures.

The outer member 312 can be coupled to the frame 302 at a second location, axially spaced from the first location. For example, in the illustrated embodiment, the inner member 314 is secured to the frame 302 near the distal or inflow end 306 of the frame and the outer member 312 is secured to the frame 302 closer to or at the proximal or outflow end 308 of the frame, such as via a fastener 336 (FIG. 11), which can be, for example, a rivet or a pin. The fastener 336 is affixed to and extends radially from the outer member 312 through corresponding apertures at a junction of two overlapping struts 304 and can serve as a pivot pin around which the two struts 304 can pivot relative to each other and the outer member 312. A nut can be mounted on each fastener 336 to retain the fastener within the corresponding apertures. The expansion and locking mechanism 310 can be coupled to the frame 302 at any two axially spaced, circumferentially aligned locations on the frame.

In alternative embodiments, the inner member and/or outer member 314, 312 need not comprise fasteners 334, 336 and can be coupled to the frame 302 via other means of attachment such as welding, adhesives, etc.

As shown in FIG. 9, the inner member 314 can be axially movable relative to the outer member 312 in a proximal direction, as shown by arrow 338, and in a distal direction, as shown by arrow 340. As such, because the inner member 314 and the outer member 312 are secured to the frame 302 at axially spaced locations, moving the inner member 314 and the outer member 312 axially relative to one another in a telescoping manner causes radial expansion and/or compression of the frame 302. For example, moving the inner member 314 proximally toward the outflow end 308 of the frame, as shown by arrow 338, while holding the outer member 312 in a fixed position and/or moving the outer member 312 distally toward the inflow end 306 of the frame can cause the frame 302 to foreshorten axially and expand radially. Conversely, moving the inner member 314 distally in the direction of arrow 338 and/or moving the outer member 312 proximally causes the frame 302 to elongate axially and compress radially.

As best shown in FIG. 11, outer member 312 can further comprise a recess 342. The recess 342 can extend through a thickness of the outer member 312 and can extend to the distal edge 344 of the outer member. The recess 342 can be configured to limit the proximal advancement of the inner member 314 within the outer member 312. For example, as the prosthetic valve 300 expands, the inner member 314 can slide relative to the outer member 312 such that the fastener 334 of the inner member 314 can slide within the recess 342. The inner member 314 can continue moving relative to the outer member 312 until the fastener 334 abuts a proximal edge 346 of the recess 342, restraining further motion of the inner member 314 relative to the outer member 312.

The locking member 316 can have a first end portion 348 and a second end portion 350. The first end portion 348 can have a circular shape in cross-section and can extend at least partially into the second bore 330 of the inner member 314. The second end portion 350 can comprise an engagement member 352 configured to engage one or more portions of the frame 302 to lock the frame 302 in the expanded configuration and prevent compression of the frame, as described in more detail below.

In the illustrated embodiment, the engagement member 352 is configured as a wedge having a base portion 354 and an apical portion 356. As shown in FIG. 12, the base portion 354 can have a first width $W_1$ that tapers to a second width $W_2$ at the apical portion 356. The base portion 354 can comprise a shoulder 358 sized to abut a distal edge 360 of the second member 314, thereby preventing movement of the locking member 316 relative to the second member 314 past a predetermined point.

As best shown in FIG. 16, the engagement member 352 can have a first side wall 362 and a second side wall 364 inclined relative to one another at an angle α, also referred to as the "wedge angle." The wedge angle α can be selected according to the following Equation 1. In some embodiments, the wedge angle can be configured to correspond with a selected prosthetic valve diameter.

$$\tan(\alpha)=\mu; \qquad\qquad \text{Equation 1:}$$

where α is the wedge angle, and ρ is the coefficient of friction between the engagement member 352 and the flanges 322 of the frame 302.

In some embodiments, the wedge angle α can be between about 0 degrees and about 10 degrees. For example, in particular embodiments, the wedge angle α can be between about 4 degrees and about 6 degrees. In some embodiments, the wedge angle α can be determined using the coefficient of friction between metals. For example, the static coefficient of wet friction for metals can be between about 0.1 to about 0.3. If the tangent of the wedge angle is less than the coefficient of friction, the locking member 316 will remain in the locked position under the radial forces applied by the native aortic annulus.

In the illustrated embodiment, the outer member 312, inner member 314, and locking member 316 can each have a substantially cylindrical configuration. This configuration can advantageously simplify manufacturing, for example, by allowing much simpler processing and machining procedures (such as Swiss-type and milling procedures) to be used. Furthermore, the telescoping movement of the members 312, 314, 316 relative to one another advantageously provides continuous valve expansion wherein the expansion and locking mechanism 310 can be easily maneuvered between the locked and unlocked configurations.

Figure 17:
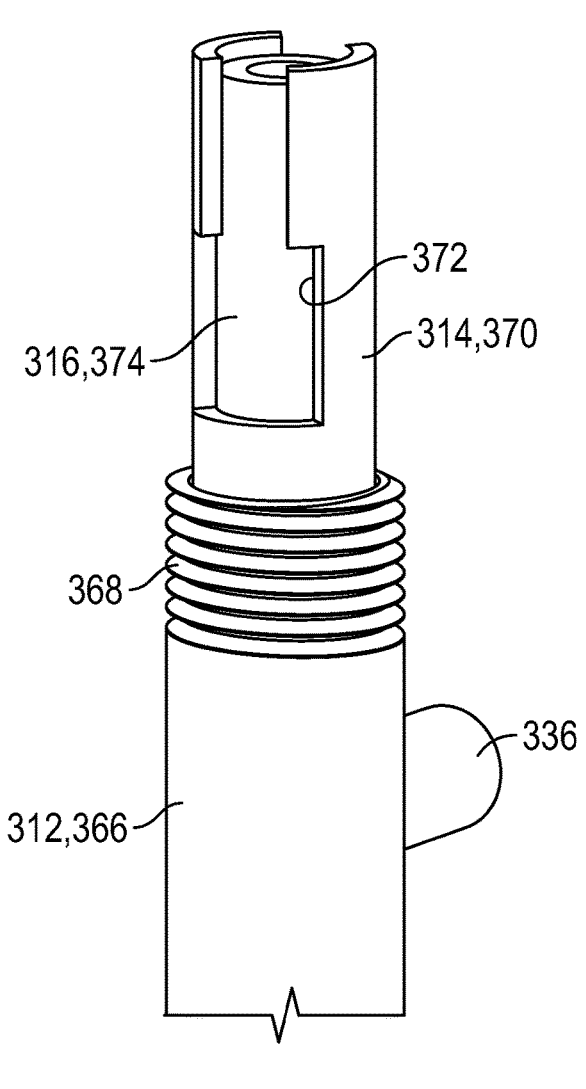
FIG. 17 is a perspective view of a portion of the expansion and locking mechanism of FIG. 11.
Figure 18:
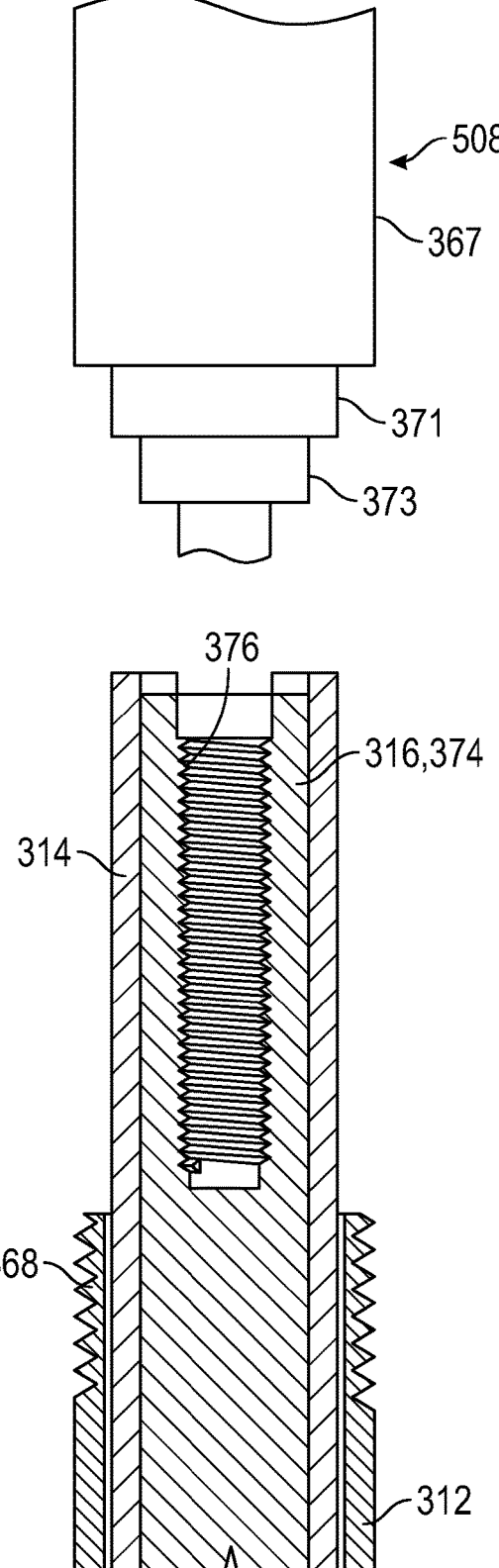
FIG. 18 is a cross-sectional side elevational view of a portion of the expansion and locking mechanism of FIG. 11 and a portion of a delivery apparatus, according to one embodiment.

As shown in FIGS. 17-18, the proximal end portion of each member 312, 314, 316 can comprise an engagement portion configured to releasably couple a corresponding actuator of a delivery apparatus, as described in more detail below. In the illustrated embodiment, the proximal end portion 366 of the outer member 312 comprises an outer engagement portion configured as a threaded portion 368, the proximal end portion 370 of the second member 314 comprises an engagement portion 372 including one or more cutouts, and a proximal end portion 374 of the locking member 316 can comprise an engagement portion configured as an inner bore including, for example, a threaded portion 376 (FIG. 18).

During delivery of the prosthetic valve 300, the expansion and locking mechanism 310 can be releasably coupled to a delivery apparatus, such as delivery apparatus 500 (FIG. 22) comprising one or more actuator assemblies 508. For example, as shown in FIGS. 23-26, an actuator assembly 508 can couple a respective expansion and locking mechanism 310 in the following exemplary manner.

Figure 24:
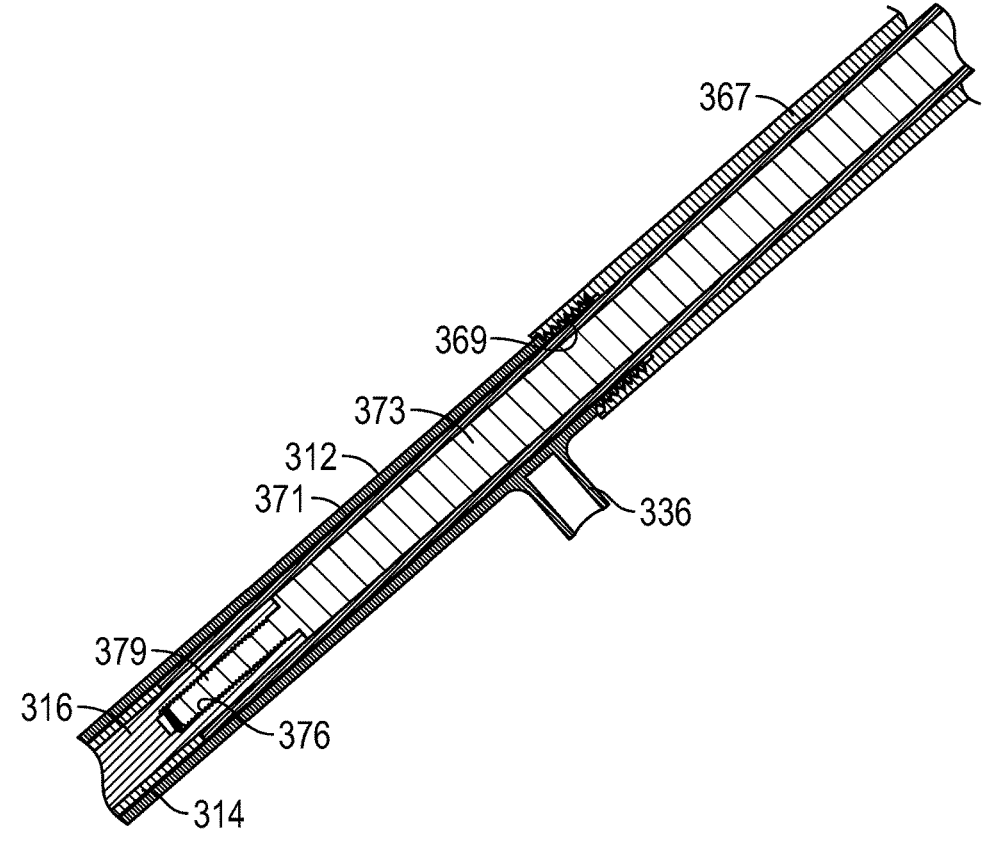
FIG. 24 is a cross-sectional view of a portion of the expansion and locking mechanism and actuator assembly of FIG. 23.

Referring now to FIG. 24, the outer threaded portion 368 (FIG. 25A) of the outer member 312 can be configured to couple a correspondingly threaded portion 369 of a first actuator 367 of the delivery apparatus. A proximal end portion 370 (FIG. 17) of the second member 314 can comprise an engagement portion 372 including one or more cutouts and configured to releasably couple a second actuator 371 extending coaxially through the first actuator 367. As best shown in FIGS. 25A-25D, the second actuator 371 can comprise one or more flexible elongated elements 375 including protrusions 377 configured to releasably couple the engagement portion 372 of the second member 314. The elongated elements 375 can be disposed, for example, at the distal end of the second actuator 371. The elongated elements can be formed by, for example, laser cutting, and the protrusions 377 can have a shape corresponding to the shape of the cutouts.

Figures 25A, 25B, 25C:
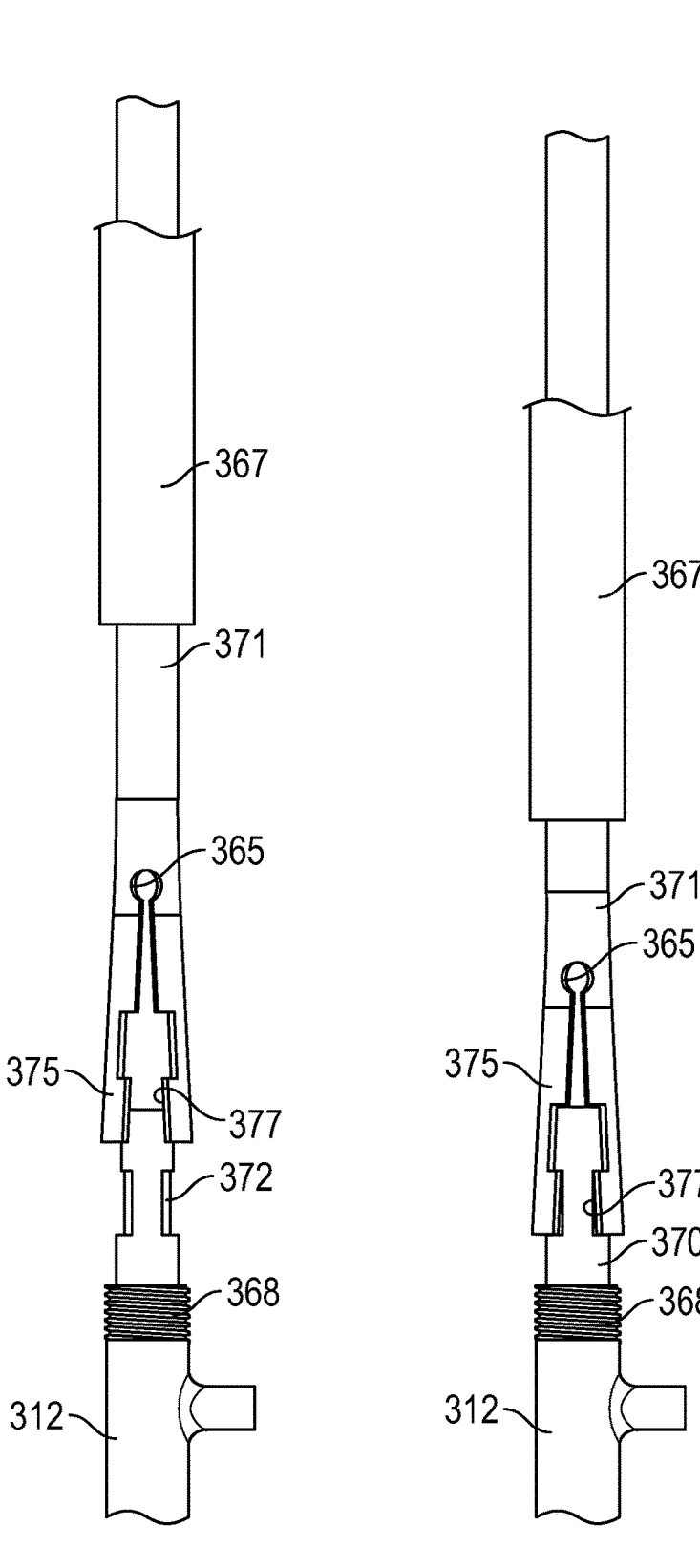
FIGS. 25A-25D are side elevational views of the actuator assembly of FIG. 23 in the process of coupling the expansion and locking mechanism of FIG. 23.
Figures 25D, 26:
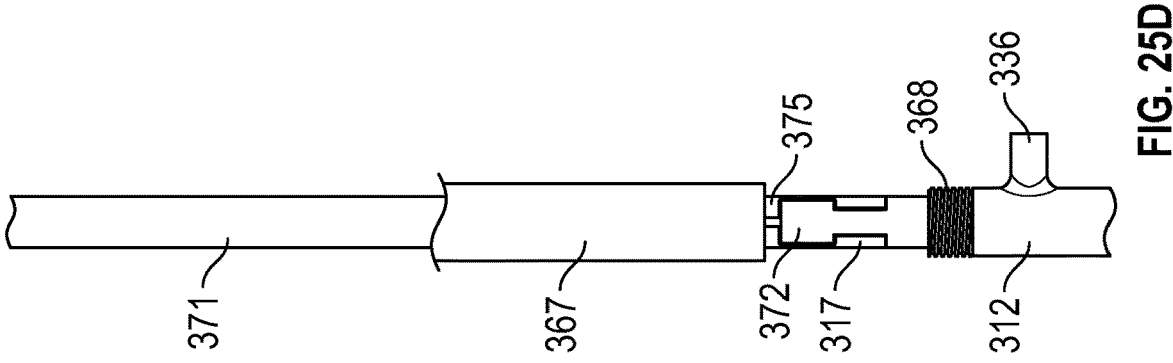
FIG. 26 is a perspective view of the expansion and locking mechanism and actuator assembly of FIG. 23.

Referring to FIGS. 25A-25D, the elongated elements 375 can be configured to bias radially outward, for example, by shape setting the elongated elements 375. The second actuator 371 can comprise a cutout 365 configured to allow the elongated elements 375 to flex outward. In order to couple the expansion and locking mechanism 310 to the delivery apparatus, the second actuator 371 can be positioned such that the protrusions 377 are disposed adjacent the cutouts of the engagement portion 372, as shown in FIG. 25C. As the first actuator 367 is advanced (e.g., distally) over the second actuator to couple the outer member 312, the elongated elements 375 are radially compressed until they sit within the cutouts, as shown in FIG. 25D, coupling the second actuator 371 to the second member 314. The first actuator 367 can continue to be advanced until the threaded portion 369 of the first actuator 367 engages the threaded portion 368 of the outer member 312, as shown in FIG. 26.

Referring again to FIG. 24, as mentioned previously, a proximal end portion 374 of the locking member 316 can comprise an engagement portion configured as an inner bore including a threaded portion 376. A third actuator 373 of the delivery apparatus can extend coaxially through the first and second actuators 367, 371 and can have a correspondingly threaded portion 379 configured to releasably couple the threaded portion 376 of the locking member 316.

The first, second, and third actuators 367, 371 and 373 can form an actuator assembly 508. Each actuator assembly 508 can be releasably coupled to and control operation of a respective expansion and locking mechanism 310. Each actuator assembly 508 can be coupled to a handle 504 of the delivery apparatus and the components of the actuator assembly (e.g., actuators 367, 371, 373) can be axially movable relative to one another to cause corresponding axial movement of the first, second, and locking members 312, 314, 316 relative to one another, as further described below.

In other embodiments, the engagement portions can have other configurations that permit the first, second, and locking members 312, 314, 316 to be releasably coupled to the delivery apparatus. For example, in some embodiments, the engagement portion of the locking member 316 can comprise a magnetic material and the third actuator can comprise a corresponding magnet that can extend into the engagement portion.

A prosthetic valve 300 including one or more expansion and locking mechanisms 310 can be expanded in the following exemplary manner. Generally, the prosthetic valve 300 is placed in a radially compressed state and releasably coupled to a distal end portion of a delivery apparatus (such as delivery apparatus 500 shown in FIG. 22), as described above, and advanced through the vasculature of a patient to a selected implantation site (e.g., the native aortic annulus). The prosthetic valve 300 can then be deployed at the implantation site and can be expanded and locked in the expanded configuration using the expansion and locking mechanisms 310. Once a selected diameter of the prosthetic valve 300 is reached, the delivery apparatus can be uncoupled from the expansion and locking mechanisms 310 and removed from the patient's body.

Referring again to FIGS. 8-10, to deploy the prosthetic valve, the physician can actuate the delivery apparatus, which can actuate the one or more expansion and locking mechanisms 310. The second member 314 can move proximally (as shown by arrow 338) and/or the first member 312 can move distally (as shown by arrow 340) to decrease the distance between the attachment locations, causing the frame 302 to foreshorten axially and expand radially until a selected diameter is achieved.

As the frame 302 expands, the radially inner and radially outer struts 304a, 304b can pivot relative to one another, thereby pivoting the first and second flanges 322a. 322b relative to one another to define the gap G between them (see FIG. 9). Once the gap G is large enough to accommodate the engagement member 352, the physician can use the delivery apparatus to advance the locking member 316 distally until the engagement member 352 is disposed within the gap G between the first and second flanges 322a. 322b, as shown in FIG. 10.

The engagement of the engagement member 352 with the first and second flanges 322a, 322b retains the frame 302 in a locked configuration, where the frame can be further radially expanded but cannot be radially collapsed. In other words, the engagement of the engagement member 352, with the flanges 322 permits pivoting movement of the struts 304 relative to each other in a first direction to expand the frame 302 and resists pivoting movement of the struts 304 relative to each other to resist radial compression of the frame 302 from forces exerted on the frame by the surrounding anatomy.

The frictional engagement between the engagement member 352 and the flanges 322 prevents the engagement member 352 from being displaced relative to the flanges 322. For example, once the prosthetic valve has been implanted within a selected implantation site within a patient, the patient's native anatomy (e.g., the native aortic annulus) may exert radial forces against the prosthetic valve 300 that would tend to compress the frame 302. However, the frictional engagement of the engagement member 352 with the flanges 322 prevents such forces from displacing the engagement member and compressing the frame 302.

If repositioning or recapture and removal of the prosthetic valve 300 is desired, the prosthetic valve can be unlocked by retracting the locking member 316 proximally until the engagement member 352 is no longer disposed between the first and second flanges 322a, 322b, allowing the struts 304 to pivot freely relative to one another in either direction. In order to retract the locking member 316 a proximally-directed force must be applied to the locking member 316 that is greater than the force of the frictional engagement between the flanges 322 and the engagement member 352.

Figure 19:
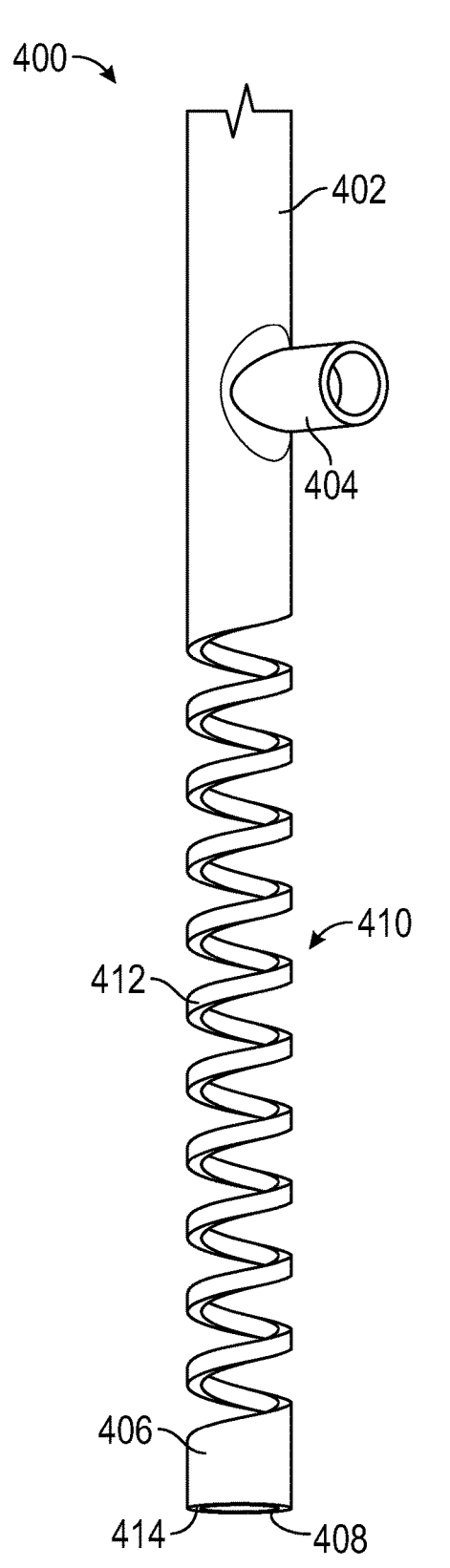
FIG. 19 is a perspective view of a portion of a second member of an expansion and locking mechanism, according to another embodiment.
Figure 20:
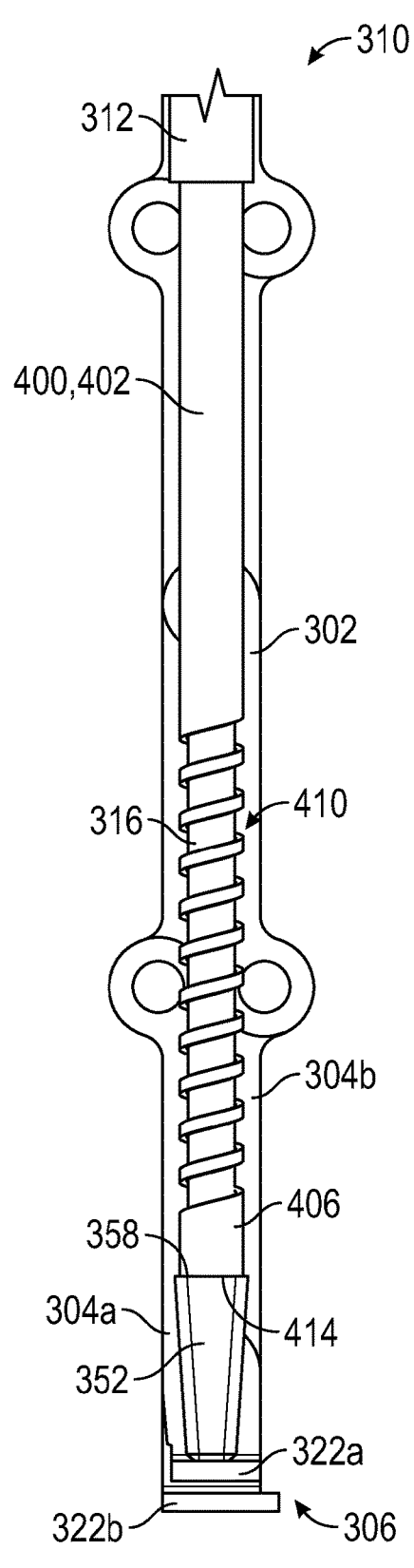
FIG. 20 is a side elevational view of a portion of a frame comprising an expansion and locking mechanism including the second member of FIG. 19, shown in a compressed configuration.
Figure 21:
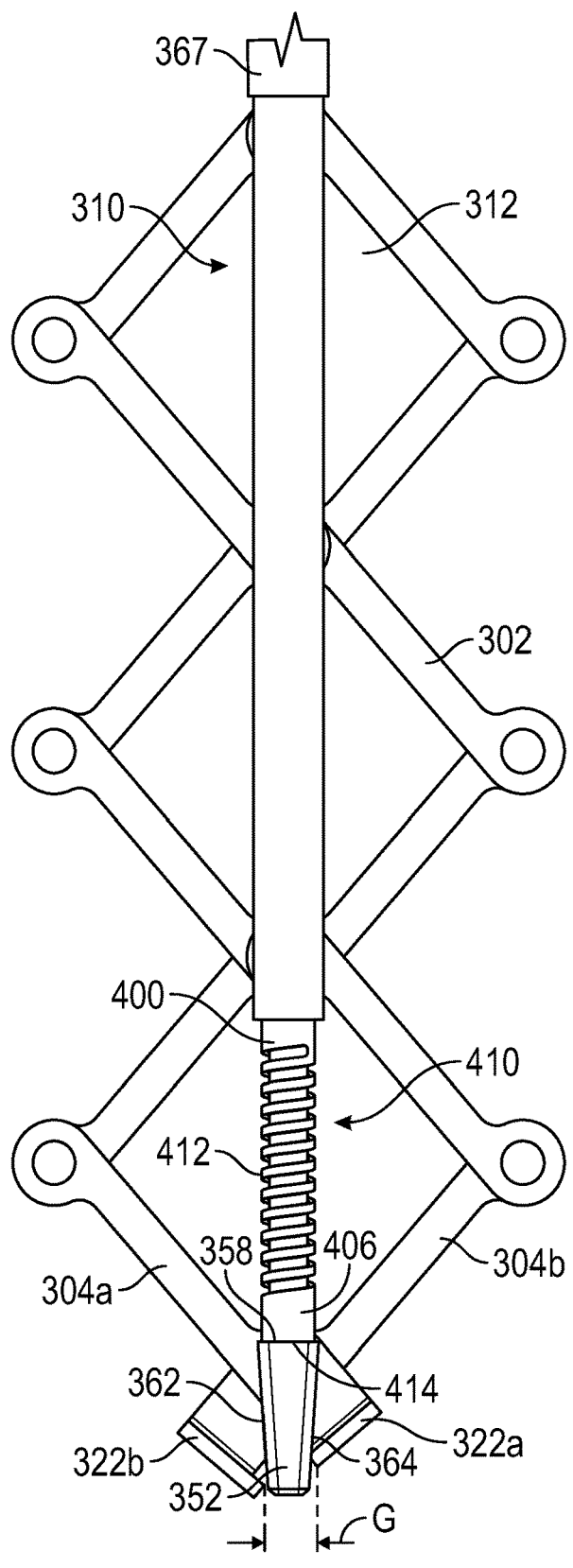
FIG. 21 is a side elevational view of a portion of the frame of FIG. 20, shown in an expanded configuration.

Referring now to FIGS. 19-21, in some embodiments, in lieu of second member 314 the expansion and locking mechanism 310 can comprise second member 400. Second member 400 can be similar to second member 314 except that second member 400 can be configured to bias the locking member 316 in a distal direction, as described in more detail below.

Referring to FIG. 19, the second member 400 can have a first end portion 402 including a fastener 404 similar to fastener 332 described above, a second end portion 406, and an inner lumen or bore 408. The second member 400 can comprise a biasing portion 410 disposed between the first and second end portions 402, 406. The biasing portion 410 can be movable between a compressed configuration and an extended configuration and can be configured to bias the second end portion 406 in a first direction, for example, toward the inflow end portion 306 of the prosthetic valve 300.

In the illustrated embodiment, the biasing portion 410 is configured as a spring 412 (such as a compression spring). In some embodiments, the spring 412 can be formed integrally with the second member 400, for example, by laser cutting a central portion of the second member 400 into a helical shape. In other embodiments, the spring 412 can be formed as a separate component and can be coupled to the first and second end portions 402, 406 of the second member 400. In other embodiments, the biasing portion 410 can have any of various configurations. For example, the biasing portion 410 can comprise a spring washer, a compressible polymeric sleeve, etc.

As shown in FIG. 20, when the expansion and locking mechanism 310 comprising second member 400 is assembled, the locking member 316 extends at least partially through the second member 400. The biasing portion 410 can be sized such that when the prosthetic valve 300 is in the compressed configuration, the biasing portion 410 is axially compressed or loaded. In the loaded state, a distal edge 414 of the second member 400 applies a proximally-directed force to the shoulder 358 of the locking member 316.

When the prosthetic valve 300 is in the compressed configuration, as shown in FIG. 20, the biasing portion 410 biases the locking member 316 distally toward the inflow end 306 such that the engagement member 352 abuts the radially extending portion 326a of the first flange 322a. As the frame 302 expands, the inner and outer struts 304a, 304b pivot relative to one another, thereby pivoting the flanges 322 relative to one another to define the gap G between them. The biasing portion 410 continues to bias the locking member 316, and therefore the engagement portion 352, distally against the first and/or second flanges 322a, 322b until the gap G is large enough to accommodate the engagement member 352, at which point the biasing portion 410 will bias the engagement member 352 into the gap G, as shown in FIG. 21.

The frictional engagement between the engagement member 352 and the flanges 322 prevents the engagement member 352 from being displaced relative to the flanges 322. For example, once the prosthetic valve has been implanted within a selected implantation site within a patient, the patient's native anatomy (e.g., the native aortic annulus) may exert radial forces against the prosthetic valve 300 that would tend to compress the frame 302. However, the frictional engagement of the engagement member 352 with the flanges 322 prevents such forces from displacing the engagement member and compressing the frame 302.

If repositioning or recapture and removal of the prosthetic valve 300 is desired, the prosthetic valve can be unlocked by retracting the locking member 316 proximally until the engagement member 352 is no longer disposed between the first and second flanges 322a, 322b, thereby allowing the struts 304 to pivot freely relative to one another in either direction. In order to retract the locking member 316 a proximally-directed force must be applied to the locking member 316 that is greater than the force of the frictional engagement between the flanges 322 and the engagement member 352 and the force of the biasing portion 410.

In some embodiments, the biasing portion 410 can be sized such that when the prosthetic valve 300 is in the expanded configuration (FIG. 21), the biasing portion 410 is in the uncompressed or unloaded configuration such that the biasing portion no longer applies a biasing force. In other embodiments, the biasing portion 410 can be sized such that w % ben the prosthetic valve 300 is in the expanded configuration, the biasing portion 410 continues to apply a biasing force in the distal direction to help retain the engagement member 352 between the flanges 322.

Figure 22:
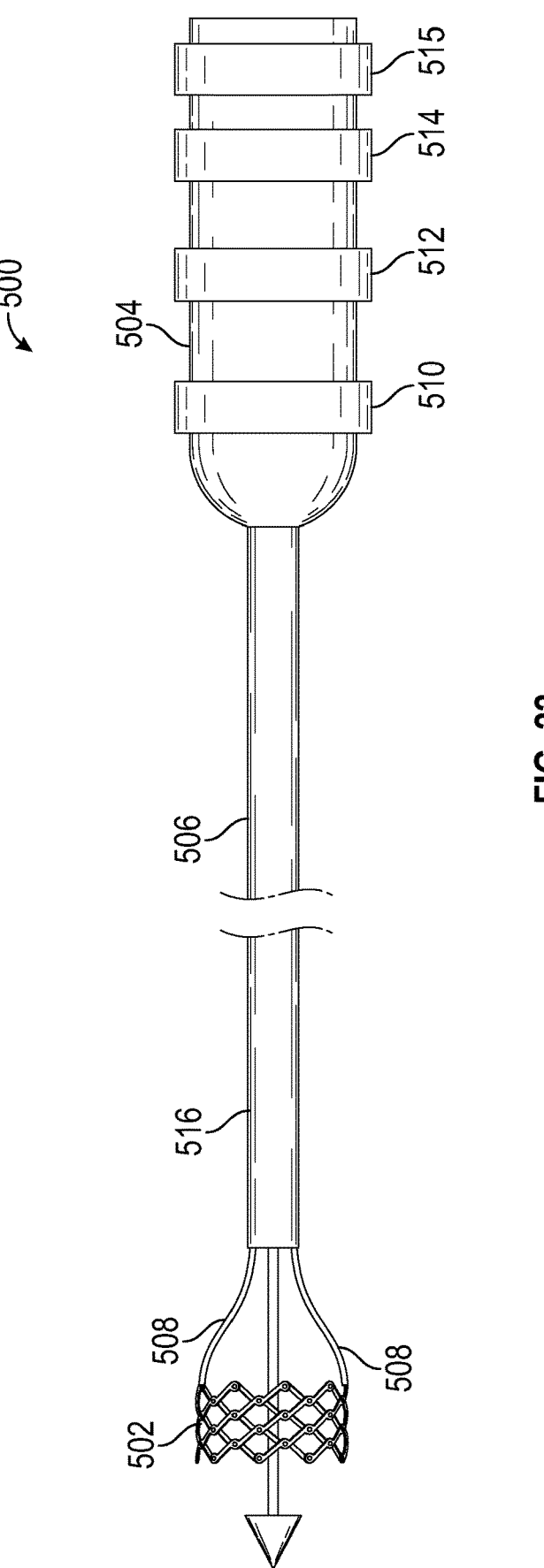
FIG. 22 is a side elevation view of a delivery apparatus for a prosthetic heart valve, according to one embodiment.
Figure 23:
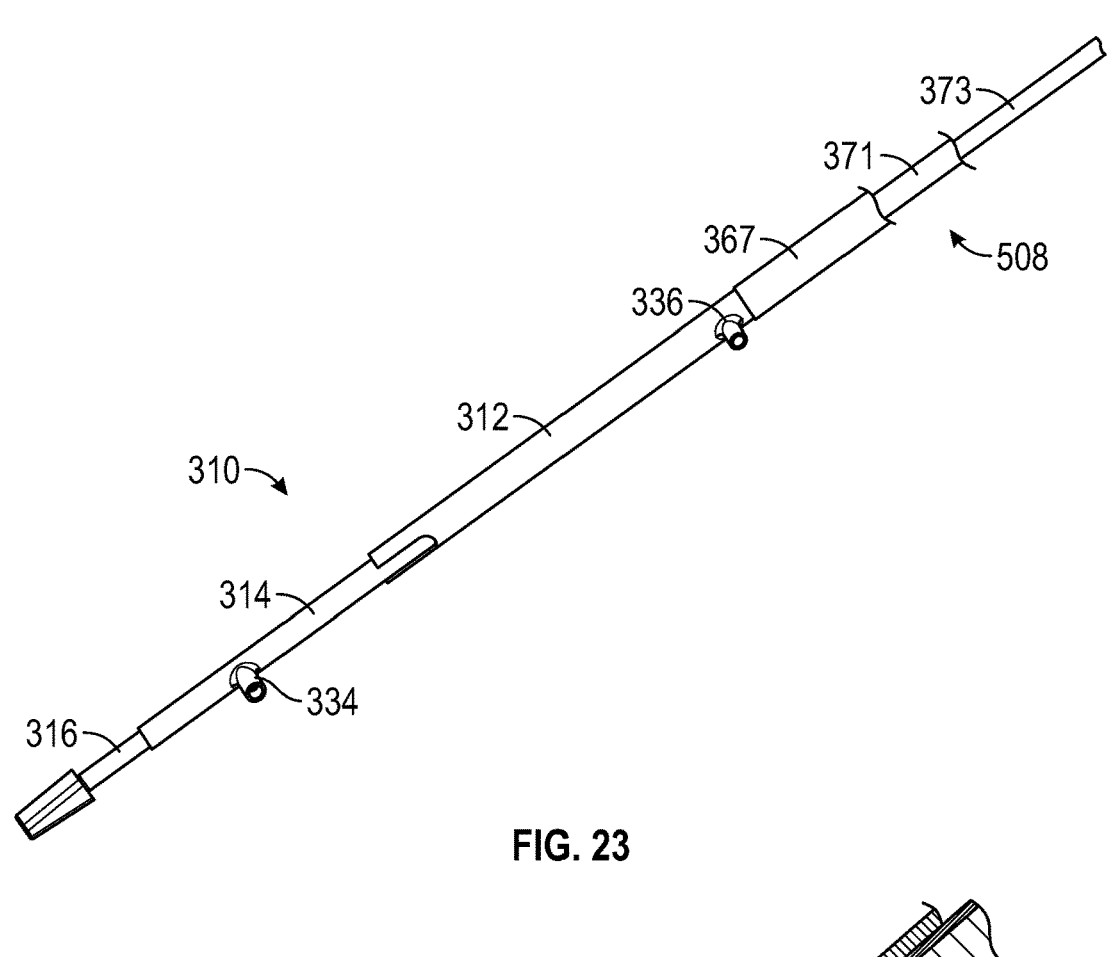
FIG. 23 is a perspective view of the expansion and locking mechanism of FIG. 11 coupled to a portion of an actuator assembly of a delivery apparatus, according to one embodiment.

FIG. 22 illustrates a delivery apparatus 500, according to one embodiment, adapted to deliver a prosthetic heart valve 502, such as the illustrated prosthetic heart valve 10, 100, or 300 described above. The prosthetic valve 502 can be releasably coupled to the delivery apparatus 500. It should be understood that the delivery apparatus 500 and other delivery apparatuses disclosed herein can be used to implant prosthetic devices other than prosthetic valves, such as stents or grafts.

The delivery apparatus 500 in the illustrated embodiment generally includes a handle 504, a first elongated shaft 506 (which comprises an outer shaft in the illustrated embodiment) extending distally from the handle 504, at least one actuator assembly 508 extending distally through the outer shaft 506. The at least one actuator assembly 508 can be configured to radially expand and/or radially collapse the prosthetic valve 502 when actuated.

Though the illustrated embodiment shows two actuator assemblies 508 for purposes of illustration, it should be understood that one actuator 508 can be provided for each actuator (e.g., each expansion and locking mechanism) on the prosthetic valve. For example, three actuator assemblies 508 can be provided for a prosthetic valve having three actuators. In other embodiments, a greater or fewer number of actuator assemblies can be present.

In some embodiments, a distal end portion 516 of the shaft 506 can be sized to house the prosthetic valve in its radially compressed, delivery state during delivery of the prosthetic valve through the patient's vasculature. In this manner, the distal end portion 516 functions as a delivery sheath or capsule for the prosthetic valve during delivery, The actuator assemblies 508 can be releasably coupled to the prosthetic valve 502. For example, in the illustrated embodiment, each actuator assembly 508 can be coupled to a respective actuator (e.g., expansion and locking mechanism 310) of the prosthetic valve 502. Each actuator assembly 508 can comprise a first actuator (e.g., first actuator 367, which can be a support tube), a second actuator (e.g., second actuator 371), and a third actuator (e.g., third actuator 373, which can be a locking tool for operating locking member 316). When actuated, the actuator assembly can transmit pushing and/or pulling forces to portions of the prosthetic valve to radially expand and collapse the prosthetic valve as previously described. The actuator assemblies 508 can be at least partially disposed radially within, and extend axially through, one or more lumens of the outer shaft 506. For example, the actuator assemblies 508 can extend through a central lumen of the shaft 506 or through separate respective lumens formed in the shaft 506.

The handle 504 of the delivery apparatus 500 can include one or more control mechanisms (e.g., knobs or other actuating mechanisms) for controlling different components of the delivery apparatus 500 in order to expand and/or deploy the prosthetic valve 10. For example, in the illustrated embodiment the handle 504 comprises first, second, third and fourth knobs 510, 512, 514, and 515.

The first knob 510 can be a rotatable knob configured to produce axial movement of the outer shaft 506 relative to the prosthetic valve 502 in the distal and/or proximal directions in order to deploy the prosthetic valve from the delivery sheath 516 once the prosthetic valve has been advanced to a location at or adjacent the desired implantation location with the patient's body. For example, rotation of the first knob 510 in a first direction (e.g., clockwise) can retract the sheath 516 proximally relative to the prosthetic valve 502 and rotation of the first knob 510 in a second direction (e.g., counter-clockwise) can advance the sheath 516 distally. In other embodiments, the first knob 510 can be actuated by sliding or moving the knob 510 axially, such as pulling and/or pushing the knob. In other embodiments, actuation of the first knob 510 (rotation or sliding movement of the knob 510) can produce axial movement of the actuator assemblies 508 (and therefore the prosthetic valve 502) relative to the delivery sheath 516 to advance the prosthetic valve distally from the sheath 516.

The second knob 512 can be a rotatable knob configured to produce radial expansion and/or contraction of the prosthetic valve 502. For example, rotation of the second knob 512 can move the first actuator (e.g., actuator 367) and the second actuator (e.g., actuator 371) relative to one another (for example, to cause corresponding movement of the outer and inner members 312, 314 relative to one another). Rotation of the second knob 512 in a first direction (e.g., clockwise) can radially expand the prosthetic valve 502 and rotation of the second knob 512 in a second direction (e.g., counter-clock wise) can radially collapse the prosthetic valve 502. In other embodiments, the second knob 512 can be actuated by sliding or moving the knob 512 axially, such as pulling and/or pushing the knob. In other embodiments, the first and second actuators can each be coupled to a respective knob such that they can be actuated independently from one another.

The third knob 514 can be a rotatable knob configured to retain the prosthetic heart valve 502 in its expanded configuration. For example, the third knob 514 can be operatively connected to a third actuator (e.g., third actuator 373) that can be releasably coupled to a locking member (e.g., locking member 316). Rotation of the third knob in a first direction (e.g., clockwise) can advance the third actuator distally to, for example, advance the engagement member 352 of locking member 316 such that it engages the flanges 322 to resist radial compression of the frame of the prosthetic valve, as described above. Rotation of the knob 514 in the opposite direction (e.g., counterclockwise) can retract the third actuator proximally to unlock the frame and allow for repositioning or recapture and removal. In other embodiments, the third knob 514 can be actuated by sliding or moving the third knob 514 axially, such as pulling and/or pushing the knob.

As shown in the illustrated embodiment, the handle 504 can include a fourth knob 515 (e.g., a rotatable knob) operatively connected to a proximal end portion of one or more of the actuators 367, 371, 373. The fourth knob 515 can be configured to, upon rotation of the knob, to decouple each of the one or more actuators from, for example, a respective component of the expansion and locking mechanism. For example, the fourth knob 515 can be operable to rotate the first actuator 367 in a direction that causes a threaded distal end portion of the first actuator to decouple from the threaded portion 368 of the outer member 312 of the expansion and locking mechanism 310. Similarly, the fourth knob 515 (or an additional knob) can be operable to rotate the third actuator 373 in a direction that causes a threaded distal end portion of the third actuator to decouple from the threaded portion 376 of the locking member 316 of the expansion and locking mechanism 310. Once the actuators have been decoupled from the prosthetic valve, the delivery apparatus 500 can be removed from the patient.

General Considerations

It should be understood that the disclosed embodiments can be adapted to deliver and implant prosthetic devices in any of the native annuluses of the heart (e.g., the pulmonary, mitral, and tricuspid annuluses), and can be used with any of various delivery approaches (e.g., retrograde, antegrade, transseptal, transventricular, transatrial, etc.).

For purposes of this description, certain aspects, advantages, and novel features of the embodiments of this disclosure are described herein. The disclosed methods, apparatus, and systems should not be construed as being limiting in any way. Instead, the present disclosure is directed toward all novel and nonobvious features and aspects of the various disclosed embodiments, alone and in various combinations and sub-combinations with one another. The methods, apparatus, and systems are not limited to any specific aspect or feature or combination thereof, nor do the disclosed embodiments require that any one or more specific advantages be present or problems be solved.

Although the operations of some of the disclosed embodiments are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed methods can be used in conjunction with other methods. Additionally, the description sometimes uses terms like "provide" or "achieve" to describe the disclosed methods. These terms are high-level abstractions of the actual operations that are performed. The actual operations that correspond to these terms may vary depending on the particular implementation and are readily discernible by one of ordinary skill in the art.

All features described herein are independent of one another and, except where structurally impossible, can be used in combination with any other feature described herein. For example, expansion and locking mechanisms 310 as shown in FIG. 11 or FIG. 20 can be used in combination with prosthetic valve 100 or with prosthetic valve 10.

As used in this application and in the claims, the singular forms "a," "an," and "the" include the plural forms unless the context clearly dictates otherwise. Additionally, the term "includes" means "comprises." Further, the term "coupled" generally means physically, mechanically, chemically, magnetically, and/or electrically coupled or linked and does not exclude the presence of intermediate elements between the coupled or associated items absent specific contrary language.

As used herein, the term "proximal" refers to a position, direction, or portion of a device that is closer to the user and further away from the implantation site. As used herein, the term "distal" refers to a position, direction, or portion of a device that is further away from the user and closer to the implantation site. Thus, for example, proximal motion of a device is motion of the device away from the implantation site and toward the user (e.g., out of the patient's body), while distal motion of the device is motion of the device away from the user and toward the implantation site (e.g., into the patient's body). The terms "longitudinal" and "axial" refer to an axis extending in the proximal and distal directions, unless otherwise expressly defined.

Additional Description of Embodiments of Interest

Clause 1. An implantable prosthetic device, comprising:

a frame movable between a radially compressed and a radially expanded configuration, the frame comprising an inflow end portion and an outflow end portion, the frame comprising a plurality of struts:

at least one expansion and locking mechanism comprising:

a first member coupled to the frame at a first location, a second member coupled to the frame at a second location spaced apart from the first location, the second member extending at least partially into the first member, a third member having a first end portion and a second end portion, the first end portion extending at least partially into the first member and the second end portion comprising an engagement portion:

wherein the plurality of struts includes a first strut and a second strut pivotably coupled to one another to form an apex, the first strut comprising a first flange and the second strut comprising a second flange; and wherein, when the frame is in the expanded configuration, advancement of the third member in a distal direction positions the engagement member between the first and second flanges such that the first and second flanges engage the engagement member to resist pivoting of the first and second struts relative to one another in a first direction to resist radial compression of the frame.

Clause 2. The implantable device of clause 1, wherein the first, second, and third members are axially movable relative to each other.

Clause 3. The implantable device of any of clauses 1-2, wherein the first and second struts are pivotably coupled at an apex positioned at the inflow end portion of the frame.

Clause 4. The implantable device of any of clauses 1-3, wherein the first and second flanges extend radially inward toward a longitudinal axis of the frame.

Clause 5. The implantable device of any of clauses 1-4, wherein expansion of the prosthetic valve causes the first and second flanges to pivot away from one another to define a gap between them.

Clause 6. The implantable device of any of clauses 1-5, wherein the engagement portion comprises a base portion and an apical portion, and wherein a thickness of the engagement portion tapers from a first thickness at the base portion to a second thickness at the apical portion, the first thickness being greater than the second thickness.

Clause 7. The implantable device of any of clauses 1-6, wherein the engagement portion comprises a shoulder configured to selectively abut a distal edge portion of the second member to prevent movement of the third member in a proximal direction past a predetermined point.

Clause 8. The implantable prosthetic device of any of clauses 1-7, wherein the first member comprises a recess extending proximally from a distal edge of the first member.

Clause 9. The implantable prosthetic device of clause 8, wherein the second member comprises a fastener extending from the surface of the second member, and wherein the fastener is configured to selectively abut a proximal edge of the recess to resist movement of the second member in a proximal direction.

Clause 10. The implantable device of any of clauses 1-9, wherein the second member comprises a biasing member movable between a compressed position and an extended position, and wherein movement of the biasing member from the compressed position to the extended position advances the third member distally.

Clause 11. The implantable device of any of clauses 1-10, wherein the first flange comprises a first axial portion having a first length, wherein the second flange comprises a second axial portion having a second length, and wherein the second length is greater than the first length.

Clause 12. The implantable device of any of clauses 1-11, wherein the first flange comprises a first radial portion having a first length, wherein the second flange comprises a second radial portion having a second length, and wherein the second length is greater than the first length.

Clause 13. An assembly, comprising:
a prosthetic heart valve comprising
a frame movable between a radially compressed and a radially expanded configuration, the frame comprising an inflow end portion and an outflow end portion, the frame comprising a first strut and a second strut comprising a first flanged portion and a second flanged portion respectively,
at least one expansion and locking mechanism comprising a first member coupled to the frame at a first location, a second member coupled to the frame at a second location spaced apart from the first location, the second member extending at least partially into the first member, and a third member comprising an engagement portion;
a delivery apparatus comprising
a handle,
a first actuation member extending from the handle and coupled to the first member, the first actuation member configured to apply a distally directed force to the first member,
a second actuation member extending from the handle and coupled to the second member, the second actuation member configured to apply a proximally directed force to the second member,
a third actuation member extending from the handle and coupled to the third member,
wherein the prosthetic heart valve is radially expandable from the radially compressed configuration to the radially expanded configuration upon application of at least one of the first distally directed force and the proximally directed force to the prosthetic heart valve via the first and second actuation members, respectively; and
wherein when the prosthetic heart valve is in the radially expanded configuration the engagement portion of the third member selectively engages the first and second flanges to prevent compression of the frame.

Clause 14. The assembly of clause 13, wherein expansion of the prosthetic valve causes the first and second flanges to pivot away from one another to define a gap between them.

Clause 15. The assembly of clause 14, wherein the third actuation member is configured to apply a distally directed force to the third member to advance the engagement portion into the gap.

Clause 16. The assembly of clause 14, wherein the third member comprises a biasing portion movable between a compressed configuration and an extended configuration, and wherein movement of the biasing portion from the compressed configuration to the extended configuration advances the engagement portion into the gap.

Clause 17. The assembly of any of clauses 13-16, wherein an outflow end portion of the first member comprises a threaded engagement portion configured to releasably couple a correspondingly threaded portion of the first actuation member.

Clause 18. The assembly of any of clauses 13-17, wherein an outflow end portion of the second member comprises one or more cutouts configured to releasably couple the second actuation member.

Clause 19. The assembly of clause 18, wherein the second actuation member comprises one or more flexible elongated elements each having a shape corresponding to a shape of a respective cutout.

Clause 20. The assembly of clause 19, wherein the flexible elongated elements are configured to bias radially outwardly.

Clause 21. The assembly of any of clauses 13-20, wherein an outflow end portion of the third member comprises an inner bore having a threaded engagement portion configured to releasably couple the third actuation member.

Clause 22. A method, comprising:
inserting a distal end of a delivery apparatus into the vasculature of a patient, the delivery apparatus releasably coupled to a prosthetic heart valve movable between a radially compressed and a radially expanded configuration, the prosthetic valve comprising
a frame comprising an inflow end portion, an outflow end portion, and a plurality of struts, and
an expansion and locking mechanism comprising a first member coupled to the frame at a first location, a second member coupled to the frame at a second location spaced apart from the first location, and a third member having a first end portion and a second end portion comprising an engagement portion;
advancing the prosthetic valve to a selected implantation site,
moving at least one of the first member distally and the second member proximally to radially expand the prosthetic valve; and
advancing the third member distally such that the engagement portion engages one or more flanges radially extending from respective struts of the plurality of struts to lock the prosthetic valve in an expanded configuration.

Clause 23. The method of clause 22, wherein as the prosthetic valve radially expands, the first and second struts pivot relative to one another to define a gap between the first and second flanges into which the engagement member can selectively extend.

Clause 24. The method of clause 22, wherein the third member comprises a biasing portion movable between a compressed position and an extended position, and wherein advancing the third member distally comprises allowing the biasing portion of the third member to expand from the compressed position to the extended position.

Clause 25. An implantable prosthetic device, comprising:
a frame movable between a radially compressed and a radially expanded configuration, the frame comprising an inflow end portion and an outflow end portion, the frame comprising a plurality of struts including a first strut and a second strut pivotably coupled to one another to form an apex, the first strut comprising a first flange and the second strut comprising a second flange;

one or more expansion and locking mechanisms comprising a first member coupled to the frame at a first location.

a second member coupled to the frame at a second location, the second member extending at least partially into the first member, a third member extending at least partially into the second member and comprising an engagement portion;

wherein the second member comprises a biasing member configured to bias the engagement portion of the third member toward the inflow end of the frame; and wherein when the frame is in the expanded configuration advancement of the third member in a distal direction via the biasing member positions the engagement member between the first and second flanges such that the first and second flanges engage the engagement member to resist pivoting of the first and second struts relative to one another in a first direction to resist radial compression of the frame.

Clause 26. The implantable device of clause 25, wherein the biasing member comprises a spring.

Clause 27. The implantable device of any of clauses 25-26, wherein the frame comprises three expansion and locking mechanisms equally spaced from each other about a circumference of the frame.

Clause 28. The implantable device of any of clauses 25-27, wherein the engagement portion comprises a wedge having a base portion and an apical portion.

Clause 29. The implantable device of clause 28, wherein the base portion comprises one or more shoulders.

Clause 30. The implantable device of clause 28, wherein the wedge comprises first and second side portions inclined relative to one another at a wedge angle.

Clause 31. The implantable device of clause 30, wherein the wedge angle is between 4 degrees and 6 degrees.

Clause 32. The implantable device of any of clauses 29-31, wherein the biasing member is configured to abut the one or more shoulders.

Clause 33. The implantable device of any of clauses 25-32, wherein the first location is adjacent the outflow end portion of the frame and the second location is adjacent the inflow end portion.

Clause 34. The implantable device of any of clauses 25-33, wherein the first and second members are axially movable relative to one another in a telescoping manner to move the frame between the radially expanded and compressed configurations.

Clause 35. The implantable device of any of clauses 25-34, wherein an outflow end portion of the first member comprises a threaded engagement portion configured to releasably couple a first actuation member of a delivery apparatus.

Clause 36. The implantable device of clause 35, wherein an outflow end portion of the second member comprises one or more cutouts configured to releasably couple a second actuation member of the delivery apparatus.

Clause 37. The implantable device of any of clauses 35-36, wherein an outflow end portion of the third member comprises an inner bore having a threaded engagement portion configured to releasably couple a third actuation member of the delivery apparatus.

Clause 38. The implantable device of any of clauses 25-37, wherein the first and second struts are pivotably coupled at an apex positioned at the inflow end portion of the frame.

Clause 39. The implantable device of any of clauses 25-38, wherein the first and second flanges extend radially inward toward a longitudinal axis of the frame.

Clause 40. The implantable device of any of clauses 25-39, wherein expansion of the prosthetic valve causes the first and second flanges to pivot away from one another to define a gap between them.

Clause 41. The implantable prosthetic device of any of clauses 25-40, wherein the first member comprises a recess extending proximally from a distal edge of the first member.

Clause 42. The implantable prosthetic device of clause 41, wherein the second member comprises a fastener extending from the surface of the second member, and wherein the fastener is configured to selectively abut a proximal edge of the recess to resist movement of the second member in a proximal direction.

Clause 43. The implantable device of any of clauses 25-42, wherein the first flange comprises a first axial portion having a first length, wherein the second flange comprises a second axial portion having a second length, and wherein the second length is greater than the first length.

Clause 44. The implantable device of any of clauses 25-43, wherein the first flange comprises a first radial portion having a first length, wherein the second flange comprises a second radial portion having a second length, and wherein the second length is greater than the first length.

Clause 45. An assembly, comprising:

a prosthetic heart valve comprising:

a frame movable between a radially compressed and a radially expanded configuration, the frame comprising an inflow end portion and an outflow end portion, the frame comprising a first strut and a second strut comprising a first flanged portion and a second flanged portion respectively, and an expansion and locking mechanism comprising a first member, a second member, and a third member, the first member coupled to the frame at a first location, the second member coupled to the frame at a second location spaced apart from the first location and comprising a biasing member configured to bias an engagement portion of the third member toward the inflow end of the frame;

a delivery apparatus comprising a handle, a first actuation member extending from the handle and coupled to the first member, the first actuation member configured to apply a distally directed force to the first member, and a second actuation member extending from the handle and coupled to the second member, the second actuation member configured to apply a proximally directed force to the second member;

wherein the prosthetic heart valve is radially expandable from the radially compressed configuration to the radially expanded configuration upon application of at least one of the first distally directed force and the proximally directed force to the prosthetic heart valve via the first and second actuation members, respectively; and wherein when the prosthetic heart valve is in the expanded configuration, advancement of the third member in a distal direction via the biasing member positions the engagement member between the first and second flanged portions such that the first and second flanged portions engage the engagement member to resist pivoting of the first and second struts relative to one another in a first direction to resist radial compression of the frame.

Clause 46. The assembly of clause 45, wherein expansion of the prosthetic valve causes the first and second flanges to pivot away from one another to define a gap between them.

Clause 47, the assembly of any of clauses 45-46, wherein an outflow end portion of the first member comprises a threaded engagement portion configured to releasably couple a correspondingly threaded portion of the first actuation member.

Clause 48. The assembly of any of clauses 45-47, wherein an outflow end portion of the second member comprises one or more cutouts configured to releasably couple the second actuation member.

Clause 49. The assembly of clause 48, wherein the second actuation member comprises one or more flexible elongated elements each having a shape corresponding to a shape of a respective cutout.

Clause 50. The assembly of clause 49, wherein the flexible elongated elements are configured to bias radially outwardly.

In view of the many possible embodiments to which the principles of the disclosure may be applied, it should be recognized that the illustrated embodiments are only preferred examples and should not be taken as limiting the scope of the disclosure. Rather, the scope of the disclosure is defined by the following claims. We therefore claim all that comes within the scope and spirit of these claims.

I claim:

1. An implantable prosthetic device, comprising:
a frame movable between a radially compressed and a radially expanded configuration, the frame comprising an inflow end portion and an outflow end portion, the frame comprising a plurality of struts;
at least one expansion and locking mechanism comprising:
a first member coupled to the frame at a first location,
a second member coupled to the frame at a second location spaced apart from the first location, the second member extending at least partially into the first member,
a third member having a first end portion and a second end portion, the first end portion extending at least partially into the first member and the second end portion comprising an engagement portion;
wherein the plurality of struts includes a first strut and a second strut pivotably coupled to one another to form an apex, the first strut comprising a first flange and the second strut comprising a second flange, and
wherein, when the frame is in the expanded configuration, advancement of the third member in a distal direction positions the engagement portion between the first and second flanges such that the first and second flanges engage the engagement member to resist pivoting of the first and second struts relative to one another in a first direction to resist radial compression of the frame.

2. The implantable device of claim 1, wherein the first, second, and third members are axially movable relative to each other.

3. The implantable device of claim 1, wherein the first and second struts are pivotably coupled at an apex positioned at the inflow end portion of the frame.

4. The implantable device of claim 1, wherein the first and second flanges extend radially inward toward a longitudinal axis of the frame.

5. The implantable device of claim 1, wherein expansion of the prosthetic device causes the first and second flanges to pivot away from one another to define a gap between them.

6. The implantable device of claim 1, wherein the engagement portion comprises a base portion and an apical portion, and wherein a thickness of the engagement portion tapers from a first thickness at the base portion to a second thickness at the apical portion, the first thickness being greater than the second thickness.

7. The implantable device of claim 1, wherein the engagement portion comprises a shoulder configured to selectively abut a distal edge portion of the second member to prevent movement of the third member in a proximal direction past a predetermined point.

8. The implantable device of claim 1, wherein the first member comprises a recess extending proximally from a distal edge of the first member.

9. The implantable device of claim 8, wherein the second member comprises a fastener extending from a surface of the second member, and wherein the fastener is configured to selectively abut a proximal edge of the recess to resist movement of the second member in a proximal direction.

10. The implantable device of claim 1, wherein the second member comprises a biasing member movable between a compressed position and an extended position, and wherein movement of the biasing member from the compressed position to the extended position advances the third member distally.

11. The implantable device of claim 1, wherein the first flange comprises a first axial portion having a first length, wherein the second flange comprises a second axial portion having a second length, and wherein the second length is greater than the first length.

12. The implantable device of claim 1, wherein the first flange comprises a first radial portion having a first length, wherein the second flange comprises a second radial portion having a second length, and wherein the second length is greater than the first length.

13. An assembly, comprising:
a prosthetic heart valve comprising
a frame movable between a radially compressed and a radially expanded configuration, the frame comprising an inflow end portion and an outflow end portion, the frame comprising a first strut and a second strut comprising a first flange and a second flange respectively,
at least one expansion and locking mechanism comprising
a first member coupled to the frame at a first location,
a second member coupled to the frame at a second location spaced apart from the first location, the second member extending at least partially into the first member, and a third member comprising an engagement portion;
a delivery apparatus comprising
a handle,
a first actuation member extending from the handle and releasably coupled to the first member, the first actuation member configured to apply a distally directed force to the first member,
a second actuation member extending from the handle and releasably coupled to the second member, the second actuation member configured to apply a proximally directed force to the second member,
a third actuation member extending from the handle and releasably coupled to the third member,
wherein the prosthetic heart valve is radially expandable from the radially compressed configuration to the radially expanded configuration upon application of at least one of the distally directed force and the proximally directed force to the prosthetic heart valve via the first and second actuation members, respectively; and wherein when the prosthetic heart valve is in the radially expanded configuration the engagement portion of the third member selectively engages the first and second flanges to prevent compression of the frame.

14. The assembly of claim 13, wherein expansion of the prosthetic valve causes the first and second flanges to pivot away from one another to define a gap between them.

15. The assembly of claim 14, wherein the third actuation member is configured to apply a distally directed force to the third member to advance the engagement portion into the gap.

16. The assembly of claim 14, wherein the third member comprises a biasing portion movable between a compressed configuration and an extended configuration, and wherein movement of the biasing portion from the compressed configuration to the extended configuration advances the engagement portion into the gap.

17. The assembly of claim 13, wherein an outflow end portion of the first member comprises a threaded engagement portion configured to releasably couple a correspondingly threaded portion of the first actuation member.

18. The assembly of claim 13, wherein an outflow end portion of the second member comprises one or more cutouts configured to releasably couple the second actuation member.

19. The assembly of claim 18, wherein the second actuation member comprises one or more flexible elongated elements each having a shape corresponding to a shape of a respective cutout, wherein each of the one or more flexible elongated elements is biased radially outwardly.

20. The assembly of claim 13, wherein an outflow end portion of the third member comprises an inner bore having a threaded engagement portion configured to releasably couple the third actuation member.

* * * * *